US011312873B2

(12) United States Patent
Boone et al.

(10) Patent No.: US 11,312,873 B2
(45) Date of Patent: *Apr. 26, 2022

(54) AROMATIC ENOL ETHER PAINT ADDITIVES

(71) Applicant: Eastman Chemical Company, Kingsport, TN (US)

(72) Inventors: Matthew Allen Boone, Kingsport, TN (US); Dustin John Czirr, Johnson City, TN (US)

(73) Assignee: Eastman Chemical Company

( * ) Notice: Subject to any disclaimer, the term of this patent is extended or adjusted under 35 U.S.C. 154(b) by 0 days.

This patent is subject to a terminal disclaimer.

(21) Appl. No.: 16/559,880

(22) Filed: Sep. 4, 2019

(65) Prior Publication Data

US 2021/0062016 A1 Mar. 4, 2021

(51) Int. Cl.
| | |
|---|---|
| C09D 7/63 | (2018.01) |
| C09D 7/65 | (2018.01) |
| C07C 43/166 | (2006.01) |
| C08K 5/06 | (2006.01) |
| C08L 9/04 | (2006.01) |
| C08L 9/08 | (2006.01) |
| C08L 33/14 | (2006.01) |

(52) U.S. Cl.
CPC .............. *C09D 7/63* (2018.01); *C07C 43/166* (2013.01); *C08K 5/06* (2013.01); *C08L 9/04* (2013.01); *C08L 9/08* (2013.01); *C08L 33/14* (2013.01); *C09D 7/65* (2018.01)

(58) Field of Classification Search
CPC .................................................. C07C 43/166
See application file for complete search history.

(56) References Cited

U.S. PATENT DOCUMENTS

| | | |
|---|---|---|
| 2,578,724 A | 12/1951 | Mertzweiller |
| 4,248,957 A | 2/1981 | Sander et al. |
| 4,839,413 A | 6/1989 | Kiehlbauch et al. |
| 4,927,876 A | 5/1990 | Coogan et al. |
| 4,939,233 A | 7/1990 | Jenkins et al. |
| 4,946,932 A | 8/1990 | Jenkins |
| 5,053,556 A | 10/1991 | Ohnishi |
| 5,137,961 A | 8/1992 | Goos et al. |
| 5,247,040 A | 9/1993 | Amick et al. |
| 5,296,530 A | 3/1994 | Bors et al. |
| 5,484,849 A | 1/1996 | Bors et al. |
| 6,451,380 B1 | 9/2002 | Speece, Jr. et al. |
| 6,743,748 B2 | 6/2004 | Mizuno et al. |
| 7,208,545 B1 | 4/2007 | Brunner et al. |
| 9,932,486 B1 | 4/2018 | Cogar et al. |
| 2006/0089415 A1 | 4/2006 | Monte et al. |
| 2009/0035696 A1 | 2/2009 | Matsuoka |
| 2009/0076311 A1 | 3/2009 | Sato et al. |
| 2012/0157609 A1 | 6/2012 | Maddox et al. |
| 2012/0289721 A1 | 11/2012 | End et al. |
| 2015/0239816 A1 | 8/2015 | Zaragoza Doerwald et al. |

FOREIGN PATENT DOCUMENTS

| | | |
|---|---|---|
| CN | 109 721 477 A | 5/2019 |
| EP | 0 492 847 A2 | 7/1992 |
| EP | 2 050 784 A1 | 4/2009 |
| JP | S60 178840 A | 9/1985 |
| JP | S63 10153 A | 1/1988 |
| JP | H02 1868 A | 1/1990 |
| JP | 2003/327855 A | 11/2003 |
| WO | WO 2007/094922 A2 | 8/2007 |
| WO | 2011/042652 A1 | 4/2011 |
| WO | 2017/176504 A1 | 12/2017 |

OTHER PUBLICATIONS

USPTO Office Action dated Apr. 6, 2020 received in co-pending U.S. Appl. No. 16/559,842.
USPTO Notice of Allowance dated Nov. 1, 2019 received in co-pending U.S. Appl. No. 16/559,977.
USPTO Notice of Allowance dated Dec. 10, 2019 received in co-pending U.S. Appl. No. 16/559,977.
USPTO Notice of Allowance dated Nov. 1, 2019 received in co-pending U.S. Appl. No. 16/559,988.
USPTO Notice of Allowance dated Dec. 11, 2019 received in co-pending U.S. Appl. No. 16/559,988.
Kluge et al.; "Phosphonate Reagents for the Synthesis of Enol Ethers and One-Carbon Homologation to Aldehydes;" J. Org. Chem.; vol. 44; No. 26; 1979; pp. 4847-4852.
USPTO Office Action dated Apr. 30, 2020 received in co-pending U.S. Appl. No. 16/560,161.
Trost et al.; "Model for Asymmetric Induction in the Diels-Alder Reaction;" Journal of the American Chemical Society; vol. 102; 1980; pp. 7595-7596.
Co-pending U.S. Appl. No. 16/559,842, filed Sep. 4, 2019; Boone.
Co-pending U.S. Appl. No. 16/559,871, filed Sep. 4, 2019; Boone.
Co-pending U.S. Appl. No. 16/559,887, filed Sep. 4, 2019; Boone.
Co-pending U.S. Appl. No. 16/559,912, filed Sep. 4, 2019; Boone.
Co-pending U.S. Appl. No. 16/559,897, filed Sep. 4, 2019; Boone.
Co-pending U.S. Appl. No. 16/559,859, filed Sep. 4, 2019; Boone et al.
Co-pending U.S. Appl. No. 16/560,146, filed Sep. 4, 2019; Boone et al.
Co-pending U.S. Appl. No. 16/560,161, filed Sep. 4, 2019; Boone et al.
Co-pending U.S. Appl. No. 16/559,977, filed Sep. 4, 2019; Boone.
Co-pending U.S. Appl. No. 16/559,988, filed Sep. 4, 2019; Boone et al.

(Continued)

*Primary Examiner* — Arrie L Reuther
(74) *Attorney, Agent, or Firm* — Matthew W. Smith

(57) ABSTRACT

Disclosed are aromatic enol ethers that have utility as film-hardening additives for coating formulations. The aromatic enol ethers have particular utility as film-hardening additives for water-based coating formulations. The aromatic enol ethers provide improvements in hardness and hardness related properties such as block resistance without contributing to the volatile organic content of the composition.

9 Claims, No Drawings

(56) References Cited

OTHER PUBLICATIONS

ASTM D1544; Standard Test Method for Color of Transparent Liquids (Gardner Color Scale).
ASTM D2354-10[e1]; Standard Test Method for Minimum Film Formation Temperature (MFFT) of Emulsion Vehicles.
ASTM D4946; Standard Test Method for Blocking Resistance of Architectural Paints.
ASTM D6886; Standard Test Method for Determination of the Weight Percent Individual Volatile Organic Compounds in Waterborne Air-Dry Coatings by Gas Chromatography.
Burczyk, B. et al.; "Relations between chemical structure and surface activity I: Synthesis and properties of aqueous solutions of acetals formed from aliphatic aldehydes and monoalkyl ethers of ethylene glycols;" Tenside Detergents; 15(2); 1978; pp. 68-71.
Burczyk, B. et al.; "Surface Properties of Selected Linear and Cyclic Acetals;" Tensioactivos: Biodegradabilidad, Fis.-Quim. Apl., Jorn. Com. Esp. Deterg.; 11th; 1980; pp. 581-601.
Cohen, R. et al.; "Foam stabilizing properties of linear acetals containing oxyethylene units in their molecules;" Tenside Detergents; 18 (4); 1981; pp. 202-205.
Duchene, A. et al.; "Alxoxyméthyltributylétains précurseurs d'alcoxyméthyllithiums : application à la synthèse de monoéthers d'α-glycols et à l'homologation de cétones en aldéhydes;" Bulletin De La Societe Chimique De France; 1985; No. 5; pp. 787-792.
Getzkin, AJ. et al.; "Synthesis of Some Symmetrical Aldehyde Glycol Monoether Acetals;" Journal of the American Pharmaceutical Association, Scientific Edition; 49; 1960; pp. 746-750.
Kanno, T. et al.; "Oxygenation of Aromatic Vinyl Ethers. A Noticeable Formation of Epoxides and Reaction Mechanism;" Bull. Chem. Soc. Jpn.; 54; 1981; pp. 2330-2336.
Moszner, N. et al.; "Reaction behavior of monomeric β-ketoesters. 2. Synthesis, characterization and polymerization of methacrylate group containing enamines;" Polymer Bulletin; 32; pp. 419-426; (1994).
Presidential Green Chemistry Challenge: 2005 Designing Greener Chemical Award; Archer Daniels Midland Company; Archer RC™: A Nonvolatile, Reactive Coalescent for the Reduction of VOCs in Latex Paints; United States Environmental Protection Agency; Accessed via the web on Jun. 6, 2018; htttbs://www.epa.gov/greenchemistry/presidential-green-chemistry-challenge-2005-designing-greener-chemicals-award.
Robinson, M. et al.; "Epoxide ring-opening and Meinwald rearrangement reactions of epoxides catalyzed by mesoporous aluminosilicates;" Organic & Biomolecular Chemistry; 2009; 7; pp. 2559-2564.
Safa, K. et al.; "1,4-bis[2,2-bis(trimethylsilyl)ethenyl]benzene: Regioselective ring opening of its a,B-eposybix(silane) with some nucleophiles;" Journal of Organometallic Chemistry; 694; 20019; pp. 1907-1911.
Smith, O.W. et al.; "New vinyl ester monomers for emulsion polymers;" Progress in Organic Coatings; 22; 1993; pp. 19-25.
Sokolowski, A. et al.; "Acetals and Ethers. Part IV*. Synthesis of Acetals from Aliphatic Aldehydes and Monoalkyl Ether of Ethylene Glycols;" Polish Journal of Chemistry (formerly Roczniki Chemii); 53(4); 1979; pp. 905-912.
Sokolowski, A. et al.; "Statistical Evaluation of the Influence of Linear Acetal Structures on Their Adsorption at the Aqueous Solution-Air Interface;" Comunicaciones presentadas a las XII Jornadas del Comite Espanol de la Detergencia; Asociacion De Investigacion De Detergentes, Tens; 1981; pp. 491-507.
USPTO Notice of Allowance dated Aug. 10, 2020 received in co-pending U.S. Appl. No. 16/559,842.
USPTO Office Action dated Jun. 10, 2020 received in co-pending U.S. Appl. No. 16/559,871.
USPTO Notice of Allowance dated Sep. 30, 2020 received in co-pending U.S. Appl. No. 16/559,871.
USPTO Notice of Allowance dated Jun. 24, 2020 received in co-pending U.S. Appl. No. 16/559,887.
USPTO Office Action dated Jun. 10, 2020 received in co-pending U.S. Appl. No. 16/559,912.
USPTO Notice of Allowance dated Sep. 16, 2020, received in co-pending U.S. Appl. No. 16/559,912.
USPTO Office Action dated Jun. 1, 2020 received in co-pending U.S. Appl. No. 16/559,897.
USPTO Notice of Allowance dated Aug. 17, 2020 received in co-pending U.S. Appl. No. 16/560,161.

AROMATIC ENOL ETHER PAINT ADDITIVES

FIELD OF THE INVENTION

This application relates to chemistry generally. In particular, this application relates to enol ethers and more particularly to aromatic enol ethers. More particularly, this invention relates to aromatic enol ethers and their use as additives for paints and coatings.

BACKGROUND OF THE INVENTION

Typical waterborne paints consist of a latex polymer in water emulsion and additives to enhance properties such as film formation, freeze-thaw resistance, application ease, rheological properties, and pigments to provide opacity and color. Historically in such paints, the polymer had a relatively high glass-transition temperature (Tg), often in the range of 20° C. or higher. Many of the additives selected were volatile and therefore evaporated out of the film during the drying process. When the water and additives evaporated, the resulting paint film exhibited properties such as weatherability, block and print resistance, scrub resistance, dirt pick up resistance and the like, due in part to the high Tg of the latex polymer remaining in the film.

Due to regulatory restrictions limiting the amount of volatile organic materials used in paints and coatings, paint companies have been forced to modify their formulations. Many have adopted the use of softer latexes with Tg in the range of 5° C. to below 0° C. that will more readily form a film. In addition, many have also begun to use non-volatile additives which remain in the film after drying. Both approaches have yielded resulting paint films that are softer than desired for good performance. These softer coatings can have various undesirable performance characteristics such as reduced block and print resistance, poor scrub resistance, increased dirt pick up, and the like.

Attempts have been made in the past to introduce additives, often promoted as "reactive coalescents" which could increase the hardness of paint films. For example, some were based on polyunsaturated fatty acid derivatives which in theory could auto-crosslink in the presence of oxygen. Potential shortcomings for these types of materials include slow hardness development due to the minimal crosslinking at low levels of incorporation, the potential for color development, and the fact that driers may be required to promote cross-linking.

Reactive diluents may also be used to create crosslinks in a latex film. They are typically part of a two-component system; the reactive diluent contains reactive groups which react with pendant-functional groups on the latex polymer backbone such as a carbonate, epoxide, isocyanate, isopropenyl, carboxylic acid, allyl groups, acetoacetoxy or amine groups. However, these reactive systems may yellow over time, compromising coating appearance. Some reactive systems require a trigger such as UV light exposure or heat for effective crosslinking that is impractical for the consumer to implement. Furthermore, it is difficult to formulate a two-component reactive system into a single formulation and maintain the shelf-stability of the formulation prior to application.

There is a need for paint additives that react during the paint film formation process, yield films having better block or print resistance, scrub resistance, weatherability and/or solvent resistance as compared to films obtained from paint compositions without such additives, and do not contribute to the VOC of the paint formula. In particular, a need exists for waterborne coating compositions which may be formulated as a single, shelf-stable, self-curing composition which produces desirable properties in the resulting cured coating.

Other beneficial features of a good reactive film-hardening aid include low water solubility, ease of addition to paint formulations, compatibility with multiple formulations, high coalescing efficiency, low freezing point, low foaming and good hydrolytic stability. A desirable reactive film-hardening aid will be compatible with most latex polymers, is easily added to formulations, has low volatility and odor, and provides good color development properties.

SUMMARY OF THE INVENTION

The Invention is set forth in the appended claims.
The present application relates to an enol ether compound according to Formula I:

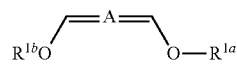

wherein:
A is $(C_{8-20})$ alkylaryl;
$R^{1a}$ and $R^{1b}$ are independently

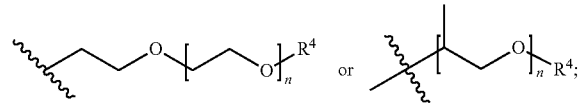

each $R^4$ is independently $(C_{1-12})$alkyl, or $-C(O)R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

The present application also relates to an enol ether compound according to Formula II:

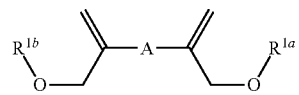

wherein:
A is $(C_{8-20})$ aryl;
$R^{1a}$ and $R^{1b}$ are independently

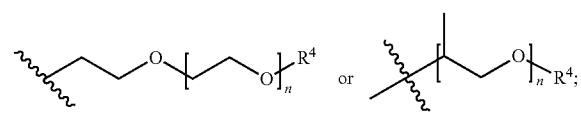

each $R^4$ is independently $(C_{1-12})$alkyl, or $-C(O)R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

The present application also relates to an enol ether compound according to Formula III:

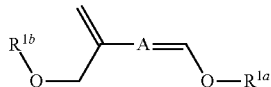

wherein:
A is $(C_{8-20})$ alkylaryl;
$R^{1a}$ and $R^{1b}$ are independently

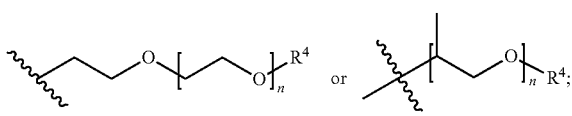

each $R^4$ is independently $(C_{1-12})$alkyl, or $-C(O)R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

The aromatic enol ethers of Formulas I, II and III have particular utility as film-hardening additives for water-based coating formulations. Such additives may also assist with enhancing the film formation (coalescing) process.

DETAILED DESCRIPTION

Definitions

In this specification and in the claims that follow, reference will be made to a number of terms, which shall be defined to have the following meanings.

"Alkyl" means an aliphatic hydrocarbon. The alkyl can specify the number of carbon atoms, for example $(C_{1-5})$ alkyl. Unless otherwise specified, the alkyl group can be unbranched or branched. In some embodiments, the alkyl group is branched. In some embodiments, the alkyl group is unbranched. Non-limiting examples of alkanes include methane, ethane, propane, isopropyl (i.e., branched propyl), butyl, and the like.

"Alkenyl" means an aliphatic hydrocarbon with one or more unsaturated carbon-carbon bonds. The alkenyl can specify the number of carbon atoms, for example $(C_{2-12})$ alkenyl. Unless otherwise specified, the alkyl group can be unbranched or branched. In some embodiments, the alkyl group is branched. In some embodiments, the alkyl group is unbranched. Non-limiting examples of alkanes include ethenyl, propenyl, butenyl, hexa-3,5-dienyl, and the like.

"Alcohol" means a chemical containing one or more hydroxyl groups.

"Aldehyde" means a chemical containing one or more $-C(O)H$ groups.

"Cycloalkyl" means a cyclic hydrocarbon compound. The cycloalkyl can specify the number of carbon atoms in ring system, for example $(C_{3-8})$cycloalkyl. Non-limiting examples of cycloalkyl include cyclopropyl, cyclobutyl, cyclohexyl, and cyclooctyl.

"Aryl" means a ring system made up carbon atoms that has at least one ring that is aromatic. The carbon units making up the aryl ring may be specified, for example 5- to 9-membered aryl. Non-limiting examples of aryl include phenyl, naphthyl, 2,3-dihydro-1H-indene, and 1,2,3,4-tetrahydronaphthalene.

Values may be expressed as "about" or "approximately" a given number. Similarly, ranges may be expressed herein as from "about" one particular value and/or to "about" or another particular value. When such a range is expressed, another aspect includes from the one particular value and/or to the other particular value. Similarly, when values are expressed as approximations, by use of the antecedent "about," it will be understood that the particular value forms another aspect.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

"Chosen from" as used herein can be used with "or" or "and." For example, Y is chosen from A, B, and C means Y can be individually A, B, or C. Alternatively, Y is chosen from A, B, or C means Y can be individually A, B, or C; or a combination of A and B, A and C, B and C, or A, B, and C.

Presented herein are novel enol ethers which can be used in applications such as (but not limited to) plasticizers, diluents, wetting agents, coalescing aids and paint additives.

In some embodiments the invention is a compound according to Formula I:

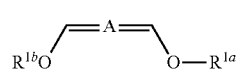

wherein: A is $(C_{8-20})$alkylaryl; $R^{1a}$ and $R^{1b}$ are independently

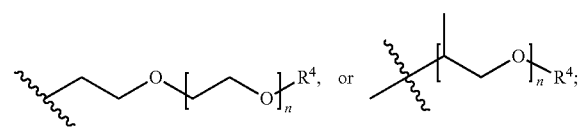

each $R^4$ is independently hydrogen, $(C_{1-12})$alkyl, $(C_{2-12})$ alkenyl or $-C(O)R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments the invention is a compound according to Formula II.

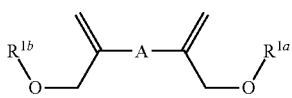
II wherein: A is $(C_{8-20})$alkylaryl; $R^{1a}$ and $R^{1b}$ are independently

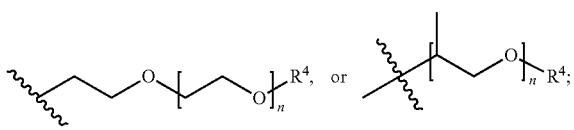

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments the invention is a compound according to Formula III:

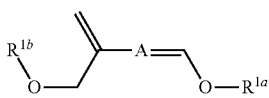
III wherein: A is $(C_{8-20})$alkylaryl; $R^{1a}$ and $R^{1b}$ are independently

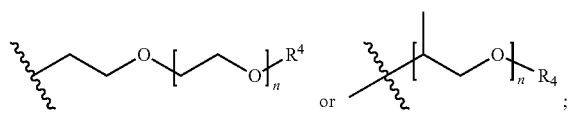

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments, A in Formulas I, II and III, is 1,2-, 1,3-, or 1,4-disubstituted phenyl. In some embodiments, each n is an integer from 1 to 3.

In some embodiments of Formulas I, II and II, each $R^4$ is hydrogen. In some embodiments, each $R^4$ is $(C_{1-12})$alkyl. In some embodiments, each $R^4$ is independently ethyl. In some embodiments, each $R^4$ is $(C_{2-12})$alkenyl. In some embodiments, each $R^4$ is —C(O)$R^5$.

In some embodiments of Formulas I, II and III, each $R^5$ is $(C_{1-12})$alkyl unsubstituted or substituted by $R^6$. In some embodiments, each $R^5$ is $(C_{1-12})$alkenyl unsubstituted or substituted by $R^6$. In some embodiments, each $R^5$ is $(C_{3-8})$cycloalkyl. In some embodiments, each $R^5$ is 5- to 9-membered aryl.

In some embodiments of Formulas, I, II and III, each n is an integer from 1 to 2. In some embodiments, each n is an integer from 1 to 3. In some embodiments, each n is an integer from 1 to 4. In some embodiments, each n is an integer from 1 to 5. In some embodiments, n is an integer from 1 to 6. In some embodiments, n is an integer from 1 to 7. In some embodiments, n is an integer from 1 to 8. In some embodiments, n is an integer from 1 to 9. In some embodiments, n is an integer from 1 to 10. In some embodiments, n is an integer from 1 to 11. In some embodiments, n is an integer from 1 to 12. In some embodiments, n is an integer from 1 to 13. In some embodiments, n is an integer from 1 to 14. In some embodiments, n is an integer from 1 to 15.

In some embodiments, the compounds of Formulas I, II and III have a volatile organic content of less than 50 wt % according to ASTM D6886. In some embodiments, the volatile organic content is less than 30 wt %. In some embodiments, the volatile organic content is less than 10 wt %. In some embodiments, the volatile organic content is less than 5 wt %. In some embodiments, the volatile organic content is less than 3 wt %. In some embodiments, the volatile organic content is less than 2 wt %. In some embodiments, the volatile organic content is less than 1 wt %. In some embodiments, the volatile organic content is less than 0.8 wt %.

Compositions

The compounds disclosed in the present application exhibit a low volatile organic content (less than 50 wt %, but as low as 0.7 wt % according to ASTM D6886) and are desirable for use in coating compositions.

The enol ether compounds disclosed in the present application exhibit a low volatile organic content (less than 50 wt %, but as low as 0.7 wt % according to ASTM D6886). The enol ethers can be used as reactive film-hardening compounds. Reactive film-hardening compounds react with components in coating compositions to form crosslinks in the films providing improved film properties. When we say that the enol ether compounds of this invention can be used as reactive film-hardening additives, we mean when added to a coating composition, that a harder film is obtained upon curing the composition than is obtained in the absence of the invention enol ether additives, or that the coating composition exhibits a higher gel fraction than in the absence of the enol ether additive, or that both coating composition hardness and increased gel fraction properties are improved by the addition of the enol ether reactive film-hardening additives.

Not wishing to be bound by any theory, the increase in hardness observed in a coating that contains the enol ether additives described herein may be the result of a chemical reaction, so that the additives described herein may be described as "reactive" enol ether film-hardening additives.

The materials described herein can also facilitate the individual latex particles coming together to form a continuous film at a given temperature by reducing the minimum film-forming temperature (MFFT) of the latex polymer.

In some embodiments, the composition comprises the compound represented by Formula I. In some embodiments, the composition comprises the compound represented Formula II. In some embodiments the composition comprises the compound represented Formula III.

The present application also includes a composition comprising the compound of Formula I or II or III, and a polymer. In some embodiments, the polymer is a latex polymer. In other embodiments, the latex polymer has a $T_g$ in the range of from about −20° C. to about 100° C. In some embodiments, the latex polymer has a $T_g$ in the range of from about 2° C. to about 60° C.

The latex polymer can be chosen from an acrylic, a vinyl acrylic, a styrene butadiene or a styrene acrylic latex polymer. In some embodiments, the latex polymer is an acrylic latex polymer. In some embodiments, the latex polymer is a vinyl latex polymer. In some embodiments, the latex polymer is styrene butadiene latex polymer. In some embodiments, the latex polymer is a styrene acrylic latex polymer.

In an embodiment of this invention, the compound of Formula I or II or III is present from about 1 to about 20 phr relative to the sum total of the polymer. In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene, a styrene acrylic latex polymer and blends thereof.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 5° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 2° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In one class of this embodiment, the compound of Formula I or II or III is present from about 1 to about 15 phr relative to the sum total of the polymer. In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 5° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 2° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In one class of this embodiment, the compound of Formula I or II or III is present from about 1 to about 10 phr relative to the sum total of the polymer. In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 5° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 2° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In one class of this embodiment, the compound of Formula I or II or III is present from about 1 to about 8 phr relative to the sum total of the polymer. In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 5° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 2° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In one class of this embodiment, the compound of Formula I or II or III is present from about 1 to about 6 phr relative to the sum total of the polymer. In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 5° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 2° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In one class of this embodiment, the compound of Formula I or II or III is present from about 1 to about 5 phr relative to the sum total of the polymer. In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 5° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 2° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In one class of this embodiment, the compound of Formula I or II or III or III is present from about 1 to about 4 phr relative to the sum total of the polymer. In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 5° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 60° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In some embodiments, the composition has a minimum film formation temperature in the range of from about −35° C. to about 2° C. In some embodiments, the polymer is a latex polymer. In some embodiments, the latex polymer has a $T_g$ in the range of from about −20° C. to about 100° C. In some embodiments, the latex polymer has a $T_g$ in the range of from about 2° C. to about 60° C. In some embodiments, the latex polymer is chosen from an acrylic, a vinyl acrylic, a styrene butadiene or a styrene acrylic latex polymer.

In one embodiment, the compound of Formula I or II or III has a volatile organic content of less than 50 wt % according to ASTM D6886. In one embodiment, the compound of Formula I or II or III has a volatile organic content of less than 40 wt % according to ASTM D6886. In one embodiment, the compound of Formula I or II or III has a volatile organic content of less than 30 wt % according to ASTM D6886. In one embodiment, the compound of Formula I or II or III has a volatile organic content of less than 20 wt % according to ASTM D6886. In one embodiment, the compound of Formula I or II or III has a volatile organic content of less than 10 wt % according to ASTM D6886. In one embodiment, the compound of Formula I or II or III has a volatile organic content of less than 5 wt % according to ASTM D6886.

In some embodiments, the compound of Formula I or II or III are aromatic enol ethers represented by the Formulas 5-19:

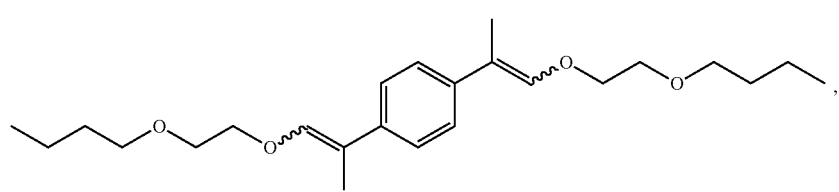

5

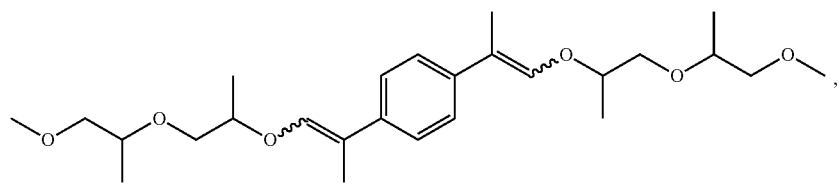

6

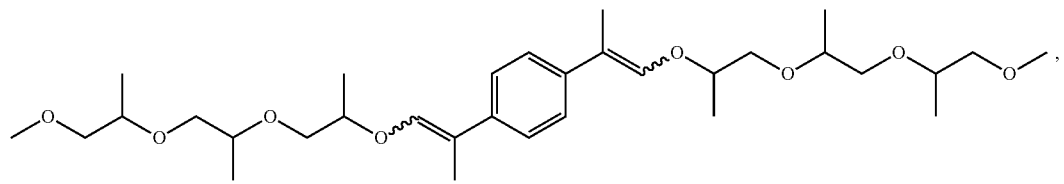
7
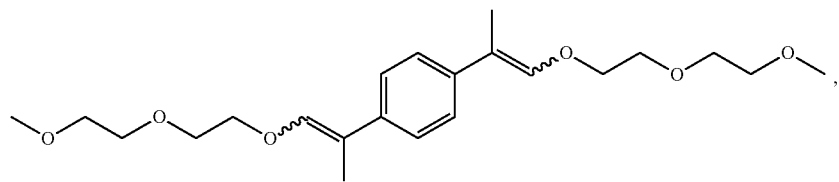
8
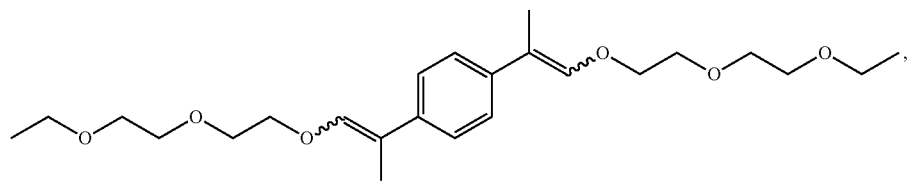
9
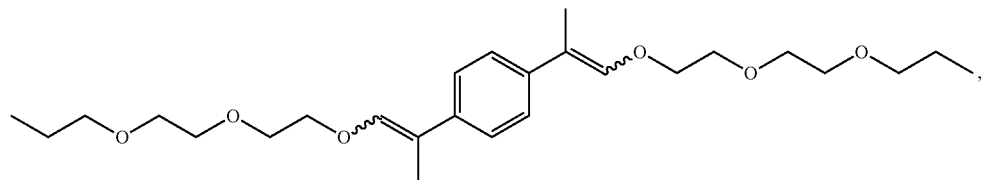
10
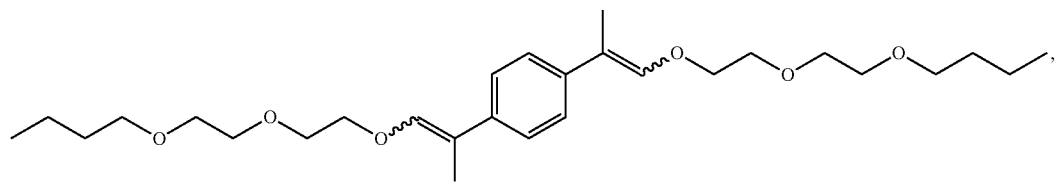
11
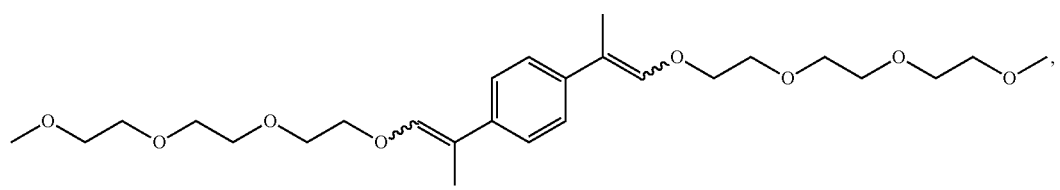
12
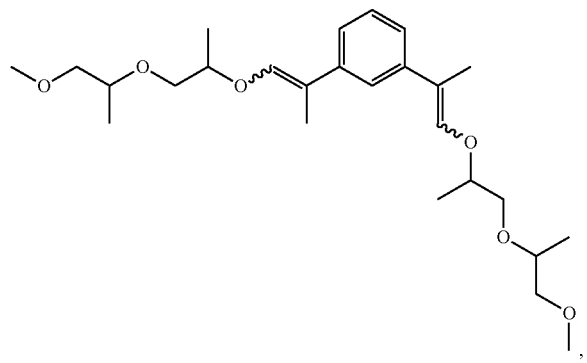
13

-continued
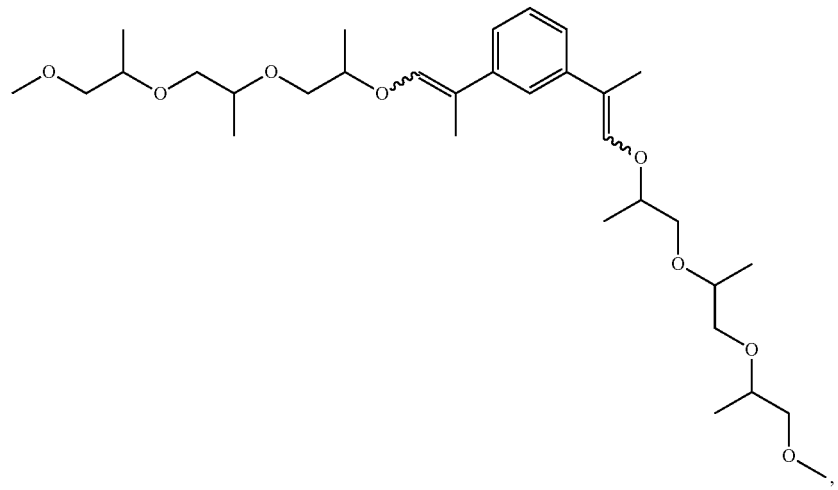
14
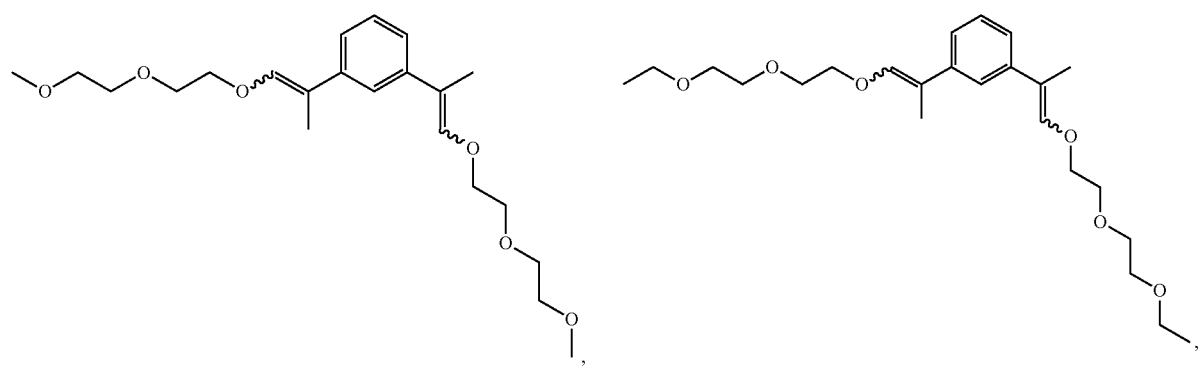
15
16
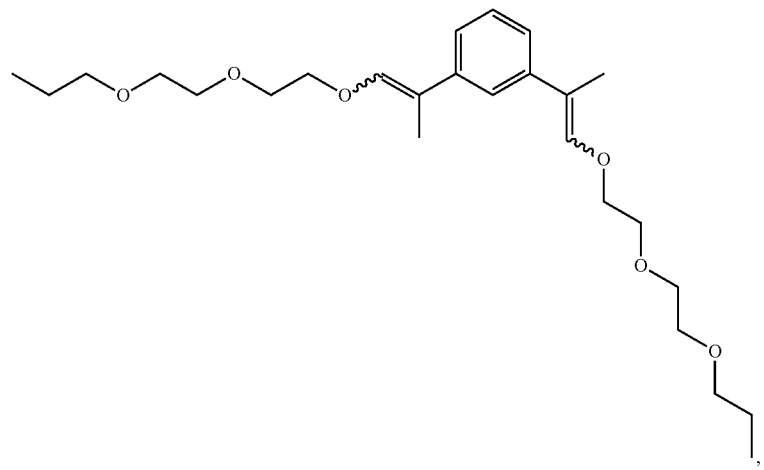
17

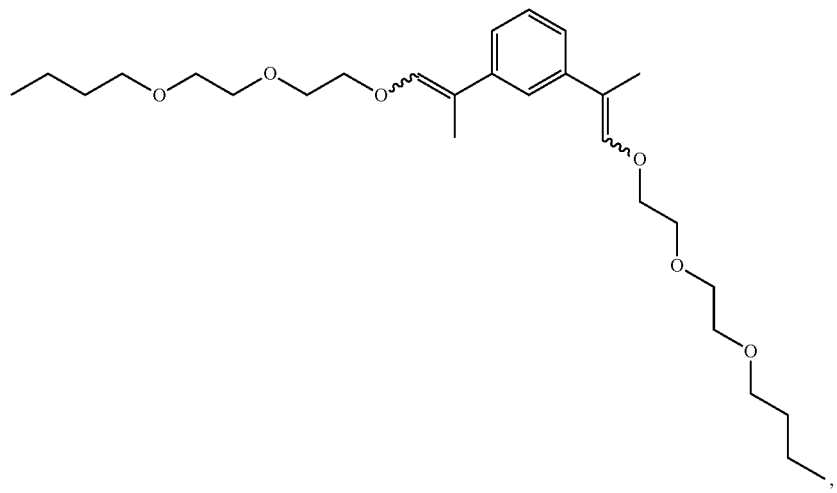

18

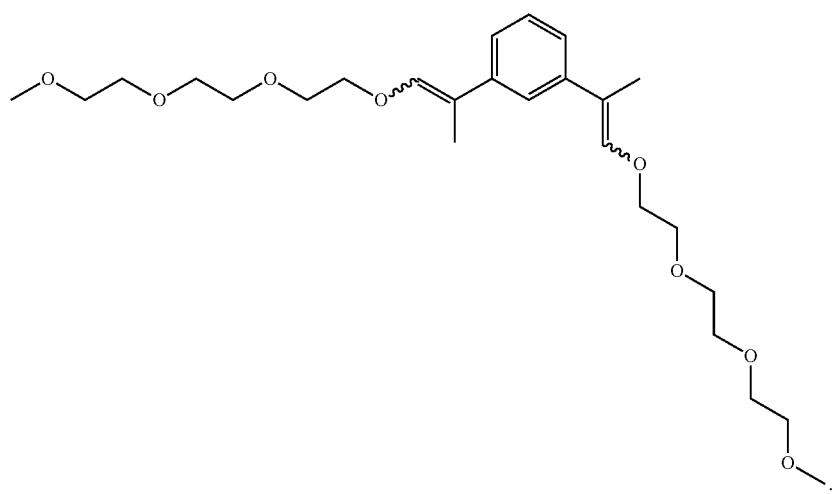

19

The aromatic enol ethers depicted by Formulas 5-19 are representative of the enol ethers claimed herein. Isomers of the enol ethers depicted by Formulas 5-19 are expected to be produced during synthesis of the enol ethers depicted by Formulas 5-19. All isomers of the enol ethers depicted by Formulas 5-19 and are within the scope of the claims set forth herein.

The compounds depicted by Formulas I, II and III of the present invention include those having a weight percent volatile content of less than 50%, as measured according to ASTM Method D6886. This test may be conducted generally by heating the sample in a forced air oven at 110° C. for 60 minutes. The weight loss after the test is deemed to result from a loss of volatiles originally present in the sample; the percent volatile present in the original sample may then be calculated. Although the cited test can be conducted on coating compositions containing other components such as latex polymers, the values cited herein may be obtained from a sample of the additive itself. The weight percent volatile of a film-hardening aid may be used herein as a yardstick to measure the amount of VOC the additive would contribute to the VOC in a particular end use such as a component of a coating composition.

Examples of the "latex polymers" useful according to the invention include aqueous vinyl polymers, which are the reaction products of one or more ethylenically unsaturated monomers. Examples of the ethylenically unsaturated monomers include, but are not limited to, styrene, methyl acrylate, methyl methacrylate, ethyl acrylate, ethyl methacrylate, butyl acrylate, butyl methacrylate, isobutyl acrylate, isobutyl methacrylate, ethylhexyl acrylate, 2-ethylhexyl methacrylate, 2-ethylhexyl acrylate, isoprene, octyl acrylate, octyl methacrylate, iso-octyl acrylate, iso-octyl methacrylate, acrylic acid, methacrylic acid, itaconic acid, crotonic acid, O-methyl styrene, vinyl naphthalene, vinyl toluene, chloromethyl styrene, hydroxyethyl (meth)acrylate, hydroxypropyl (meth)acrylate, acrylonitrile, glycidyl methacrylate, acetoacetoxyethyl methacrylate, acetoacetoxy ethyl acrylate, vinyl chloride, vinylidene chloride, vinyl acetate, butyl acrylamide, ethyl acrylamide, 2-hydroxyethyl methacrylate phosphate, and the like.

Latex emulsion polymers are well known in the art of coating compositions, and we do not intend the term to be especially limiting, although some latex emulsion polymers may be better suited as coating compositions, either inherently or in combination with the reactive film-hardening additives of the invention. Examples of commercial latex emulsion polymers useful according to the invention include Rhoplex™ SG-30, Rhoplex™ HG-74P, Rhoplex™ HG-95, Rhoplex™ SG-10M, Rhoplex™ AC2508, Ucar™ 626, and Ucar™ 379G (all available from The Dow Chemical Company), Acronal™ 296D (BASF Corp.), Aquamac™ 705 and Aquamac™ 588 (Hexion Specialty Chemicals), and the like.

In one embodiment, the polymer is a latex polymer, and the latex polymers useful according to the invention may be a homopolymer, or a copolymer of an ethylenically unsaturated monomer and one or more additional copolymerizable monomers.

The latex emulsion polymers useful according to the invention are addition polymers that may be formed via a free radical addition polymerization. In such addition polymers, the propagating species may be a free radical, and the polymer is formed in a chain-growth fashion polymerization as understood in the art. As noted, these polymers are latex emulsion polymers in which a monomer solution may be emulsified in an aqueous solution, and under agitation reacted via a free-radical polymerization process as described herein, to form latex particles.

The water-based latexes useful according to the invention may generally be prepared by polymerizing acrylic (ethylenically unsaturated) monomers. Before conducting polymerization, these ethylenically unsaturated monomers are either pre-emulsified in water/surfactant mixture or used as such.

The polymerization process of making these 'acrylic' latexes may also require an initiator (oxidant), a reducing agent, or a catalyst. Suitable initiators include conventional initiators such as ammonium persulfate, sodium persulfate, hydrogen peroxide, t-butyl hydroperoxide, ammonium or alkali sulfate, di-benzoyl peroxide, lauryl peroxide, di-tertiarybutylperoxide, 2,2-azobisisobutyronitrile, benzoyl peroxide, and the like.

Suitable reducing agents are those which increase the rate of polymerization and include, for example, sodium bisulfite, sodium hydrosulfite, sodium formaldehyde sulfoxylate, ascorbic acid, isoascorbic acid, and mixtures thereof.

Suitable catalysts are those compounds which promote decomposition of the polymerization initiator under the polymerization reaction conditions thereby increasing the rate of polymerization. Suitable catalysts include transition metal compounds and driers. Examples of such catalysts include, but are not limited to ferrous sulfate heptahydrate, ferrous chloride, cupric sulfate, cupric chloride, cobalt acetate, cobaltous sulfate, and mixtures thereof.

The latex polymers of the invention are prepared from monomers characterized as being ethylenically unsaturated monomers that can participate in addition polymerization reactions. As used herein, ethylenically unsaturated monomers may also be described as vinyl monomers. The polymers made from such monomers are addition polymers, and may be formed as emulsion polymers, also known as latexes or latex emulsions.

The latex polymers useful according to the invention may have pendant moieties, meaning that the ethylenically unsaturated monomers used to prepare the latex polymers of the invention have been reacted into an addition polymer, and that a portion of the monomers remains as a pendant moiety. Alternatively, we may say that the polymers have residues from the ethylenically unsaturated monomers of the invention, in which case we mean that the monomers have been reacted into an addition polymer via their ethylenic unsaturation, and that a portion of the monomers remains as a residue. Both these descriptions are well-known in the art of addition polymers, and the descriptions are not otherwise intended to be especially limiting.

The invention relates to the use of emulsion polymers which are also known as latexes, or as used herein, latex emulsions. In these latexes, the polymers formed may have a particle size ranging, for example, from about 80 nm to about 300 nm, or from 100 nm to 250 nm, or from 125 nm to 200 nm. The Tg of such latexes may range, for example, from about 0° C. to about 80° C., or from 15° C. to 60° C., or from 20° C. to 40° C.

The latex polymers useful according to the invention may be prepared by an emulsion free-radical polymerization of ethylenically unsaturated monomers. These latex polymers may be homopolymers or may be copolymers formed from more than one ethylenically unsaturated monomer.

Examples of ethylenically unsaturated monomers include, but are not limited to, acrylic and methacrylic acid esters such as methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, isooctyl (meth)acrylate, isodecyl (meth)acrylate, lauryl (meth)acrylate, stearyl (meth)acrylate, phenoxyethyl (meth)acrylate, methoxyethyl (meth)acrylate, benzyl (meth)acrylate, ethoxyethyl (meth)acrylate, 2-ethylhexyl (meth)acrylate, cyclopentyl (meth)acrylate and isobutyl (meth)acrylate, as well as combinations of these monomers. A combination of these monomers may be used in order to achieve an appropriate Tg or other properties for the latex emulsion polymer.

Such acrylic and methacrylic acid esters having a C1-C20 alcohol moiety are commercially available or can be prepared by known esterification processes. The acrylic and methacrylic acid ester may contain additional functional groups, such as, hydroxyl, amine, halogen, ether, carboxylic acid, amide, nitrile, and alkyl group. Such esters include carbodiimide (meth)acrylate, methyl (meth)acrylate, ethyl (meth)acrylate, butyl (meth)acrylate, isobutyl (meth)acrylate, ethylhexyl (meth)acrylate, octyl (meth)acrylate, isobutyl (meth)acrylate, allyl (meth)acrylate, and glycidyl (meth)acrylate.

Additional suitable polymerizable ethylenically unsaturated monomers include styrenic monomers. Styrenic monomers include styrene, as well as substituted styrenes such as C1-C6 alkyl ring-substituted styrene, C1-C3 alkyl alpha-substituted styrene or a combination of ring and an alpha-alkyl substituted styrene. Such styrenic polymerizable monomers include styrene, p-methyl styrene, o-methyl styrene, p-butyl styrene, alpha-methyl styrene, and combinations thereof.

In addition, vinyl esters may be used as copolymerizable mono-ethylenically unsaturated monomers, including vinyl esters of vinyl alcohol such as the VEOVA series available from Shell Chemical Company as VEOVA 5, VEOVA 9, VEOVA 10, and VEOVA 11 products. See O. W. Smith, M. J. Collins, P. S. Martin, and D. R. Bassett, Prog. Org. Coatings 22, 19 (1993).

In general, the vinyl monomers may be polymerized by a conventional emulsion free-radical initiated polymerization technique. The polymerization can be initiated by a water soluble or water-dispersible free-radical initiator, optionally in combination with a reducing agent, at an appropriate temperature, for example from 55 to 90° C. The polymerization of the monomers may be conducted batch wise, semi-batch, or in a continuous mode.

A conventional surfactant or a combination of surfactants may be used such as anionic or non-ionic emulsifier in the suspension or emulsion polymerization to prepare a polymer of the invention. Examples of such surfactants include, but are not limited to, alkali or ammonium alkylsulfate, alkylsulfonic acid, or fatty acid, oxyethylated alkylphenol, or any combination of anionic or non-ionic surfactant. A surfactant monomer may be used such as HITENOL HS-20 (which is a polyoxyethylene alkylphenyl ether ammonium sulfate available from DKS International, Inc., Japan). A list of surfactants is available in the treatise: McCutcheon's Emulsifiers & Detergents, North American Edition and International Edition, MC Publishing Co., Glen Rock, N.J. 1993. The amount of the surfactant used is usually between 0.1 to 6 wt %, based on the total weight of the monomers.

As polymerization initiators, any conventional free-radical initiator may be used such as hydrogen peroxide, t-butylhydroperoxide, ammonium or alkali sulfate, di-benzoyl peroxide, lauryl peroxide, di-tertiarybutylperoxide, 2,2'-azobisisobutyronitrile, benzoyl peroxide, and the like. The amount of the initiator is typically between 0.05 to 6.0 wt %, based on the total weight of the total monomers. A free-radical initiator may be combined with a reducing agent to form a redox initiating system. Suitable reducing agents are those which increase the rate of polymerization and include, for example, sodium bisulfite, sodium hydrosulfide, sodium, ascorbic acid, isoascorbic acid and mixtures thereof. The redox initiating system can be used at similar levels as the free-radical initiators.

In addition, in combination with the initiators and reducing agents, polymerization catalysts may be used. Polymerization catalysts are those compounds which increase the rate of polymerization by promoting decomposition of the free radical initiator in combination with the reducing agent at the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

In addition, a low level of a chain transfer agent may also be used to prepare a latex polymer useful in accordance with the invention. Suitable chain transfer agents include, but are not limited to, butyl mercaptan, n-octylmercaptan, n-dodecyl mercaptan, butyl or methyl mercaptopropionate, mercaptopropionic acid, 2-ethylhexyl 3-mercaptopropionate, n-butyl 3-mercaptopropionate, isodecylmercaptan, octadecylmercaptan, mercaptoacetic acid, haloalkyl compounds, (such as carbon tetrabromide and bromodichloromethane), and the reactive chain transfer agents described in U.S. Pat. No. 5,247,040. In particular, mercaptopropionate, allyl mercaptopropionate, allyl mercaptoacetate, crotyl mercaptopropionate and crotyl mercaptoacetate, and mixtures thereof, represent preferred chain transfer agents.

A copolymerizable monomer known to promote wet adhesion may also be incorporated into the polymer. Examples of wet adhesion promoting monomers include, but are not limited to, nitrogen-containing monomers such as t-butylaminoethyl methacrylate, dimethylaminoethyl methacrylate, diethylaminoethyl methacrylate, N,N-dimethylaminopropylmethacrylamide, 2-t-butylaminoethyl methacrylate, N,N dimethylaminoethyl acrylate and N-(2-methacryloyloxy ethyl)ethylene urea.

Water-dispersible and water-soluble polymers may also be employed as surfactants or stabilizers in accordance with the present invention. Examples of such polymeric stabilizers include water-dispersible polyesters as described in U.S. Pat. Nos. 4,946,932 and 4,939,233; water-dispersible polyurethanes as described in U.S. Pat. Nos. 4,927,876 and 5,137,961; and alkali-soluble acrylic resins as described in U.S. Pat. No. 4,839,413. Cellulosics and polyvinyl alcohols may also be used.

Surfactants and stabilizers may be used during the polymerization to control, for example, particle nucleation and growth, particle size and stability or they may be post-added to enhance stability of the latex or to modify other properties of the latex such as surface tension, wettability, and the like.

At least one ethylenically unsaturated copolymerizable surfactant may be employed, for example those possessing isopropenyl phenyl or allyl groups. Copolymerizable surfactants may be anionic, such as containing a sulfate or sulfonate group, or nonionic surfactants. Other copolymerizable surfactants include those containing polyoxyethylene alkyl phenyl ether moieties. Additional copolymerizable surfactants include sodium alkyl allyl sulfosuccinate.

The latex polymers in accordance with the invention may have a weight average molecular weight (Mw), for example, of from 1,000 to 1,000,000, as determined by gel permeation chromatography (GPC), or from 5,000 to 250,000.

The particle size for the aqueous dispersions in accordance with the invention may be, for example, from about 0.01 to about 25 µm, or from 0.05 to 1 µm, or from 0.075 to 500 µm. In an emulsion polymerization in accordance with the invention, the particle size of the latex may range, for example, from 0.01 to 5 µm.

The latex particles generally have a spherical shape, and the spherical polymeric particles may have a core portion and a shell portion or a gradient structure. The core/shell polymer particles may also be prepared in a multi-lobe form, a peanut shell, an acorn form, a raspberry form, or any other form. If the particles have a core/shell structure, the core portion may comprise from about 20 to about 80 wt % of the total weight of the particle, and the shell portion may comprise about 80 to about 20 wt % of the total weight of the particle.

The glass transition temperature (Tg) of the latex polymers in accordance with the present invention, in the absence of the reactive film-hardening additives described herein, may be up to about 100° C. In a preferred embodiment of the present invention, where a film forming at ambient temperatures of the particles is desirable, the glass transition temperature of the polymer itself may preferably be under 60° C.

The latex polymers of the invention may comprise enamine functional polymers, with the enamine functionality serving to improve the hydrolytic stability of the acetoacetoxy group. Enamine functional polymers have been described in Polymer Bulletin 32, 419-426 (1994). Additionally, enamine functional polymers are described in European Patent Application No. 0492847 A2; U.S. Pat. Nos. 5,296,530; and 5,484,849.

The coating compositions of the invention may further comprise other components commonly used in paint formulations, such as, for example, pigments, filler, rheology modifiers, thickeners, wetting and dispersing agents, deformers, freeze-thaw additives, colorants, open-time additives, driers, catalysts, crosslinkers, biocides, light stabilizers, and the like.

The driers are capable of promoting oxidative crosslinking of the unsaturated moieties and providing enhanced coating properties. Examples of commercial driers include Zirconium Hex-Cem®, Cobalt Ten-Cem®, calcium Cem-All®, Zirconium Hydro-Cem®, and Cobalt Hydro-Cure® II sold by OMG Americas of West-Lake, Ohio. Examples of driers based on unsaturated fatty alcohols include oleyl alcohol, linoleoyl alcohol, geraniol, or citronellol.

In one embodiment, the composition has a minimum film formation temperature in the range of from about −35° C. to about 60° C. In one embodiment, the composition has a minimum film formation temperature in the range of from about −35° C. to about 5° C. In one embodiment, the composition has a minimum film formation temperature in the range of from about −35° C. to about 60° C. In one embodiment, the composition has a minimum film formation temperature in the range of from about −35° C. to about 2° C.

The minimum film formation temperature of a latex is the lowest temperature at which the latex forms a practical film. MFFT can be measured using ASTM D2354. The film-forming efficiency can be determined by determining the amount of the reactive film-hardening additives required to reduce the MFFT of a latex polymer to 4.4° C., which is the lowest desirable application temperature of a paint. It is generally considered unacceptable if the amount of the reactive film-hardening additives present in a paint formulation exceeds 20% by weight based on the solids of the latex polymer. This is particularly important for a non-volatile additive since the additive will remain in the dried film and cause a detrimental effect on the coating properties such as, for example, hardness, scrub resistance, and block resistance.

EXAMPLES

This invention can be further illustrated by the following examples thereof, although it will be understood that these examples are included merely for purposes of illustration and are not intended to limit the scope of the invention unless otherwise specifically indicated. In particular more than one method to make enol ethers is available to the skilled artisan. Methods A and B are described herein.

Abbreviations mL is milliliter; wt % is weight percent; eq is equivalent(s); hrs or h is hour(s); mm is millimeter; m is meter; GC is gas chromatography; ° C. is degree Celsius; min is minute; $t_R$ is retention time; VOC is volatile organic compound; MeP is methyl palmitate; w/v is weight/volume; μL is microliter, RFHA is reactive film-hardening additive, EE is enol ether.

Method A: Dialdehyde Method

Preparation of dicarbinol [1] and 2,2'-(1,4-phenylene)dipropanal [2]

Preparation of Dicarbinol 1

KOH (49.2 g, 788 mmol) was dissolved in MeOH (400 mL) contained within a 1 L, 4-necked round-bottom flask fitted with thermocouple, overhead stirrer, and nitrogen inlet atop a reflux condenser. During the addition of KOH, internal temperature reached 60° C. and was maintained there by heating mantle. The solid di-epoxide was added over the course of 1.5 hrs. The reaction was monitored by $^1$H NMR (aliquot was taken and dissolved in DMSO-$d_6$. Once di-epoxide was completely consumed, the reaction was cooled to ambient temperature, and acetic acid (47.3 g, 788 mmol) was added dropwise. Once addition was complete, the volatiles were removed under reduced pressure using a rotary evaporator. The residue was taken up in 250 mL of toluene and then washed with 250 mL of water. The aqueous layer was back-extracted with 250 mL of EtOAc. The organics were combined, dried with $MgSO_4$ and simultaneously treated with 5 g of activated carbon. The mixture was filtered and volatiles were removed under reduced pressure using a rotary evaporator. Dicarbinol 1 was isolated as a white solid. LC-MS (Column A) $t_R$: 3.80 min (Exact mass: 254.15 m/z, found 254.2 m/z).

Preparation of 2,2'-(1,4-phenylene)dipropanal [2]

The dicarbinol 1 was then dissolved in formic acid (88%, 98.0 g) contained within a 500 mL, 4-necked round-bottom flask fitted with thermocouple, overhead stirrer, and nitrogen inlet atop a reflux condenser. The mixture was heated to 100° C. After 6 hrs, additional formic acid was added (98.0 g). After an additional 2 hrs, GC indicated >99% conversion to dialdehyde 2. The volatiles were then removed under reduced pressure using a rotary evaporator. The residue was taken up in 250 mL of toluene and then washed with a saturated solution of $NaHCO_3$. After layer separation, the organics were dried with $MgSO_4$, filtered, and then concentrated. The crude material was then Kugelrohr—distilled at 150° C./1 mm Hg to isolate the di-aldehyde 2 as a colorless oil. GC-MS $t_R$: 14.47 min (Exact mass: 190.10 m/z, found: 190.1 m/z).

Preparation of 2,2'-(1,3-phenylene)dipropanal [4]

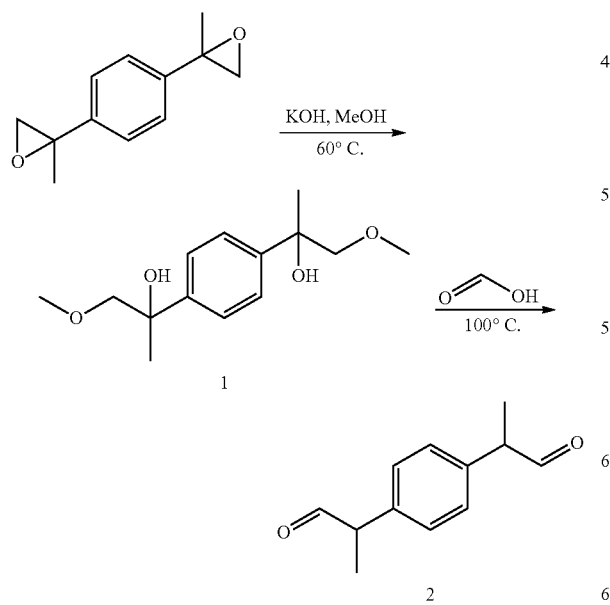

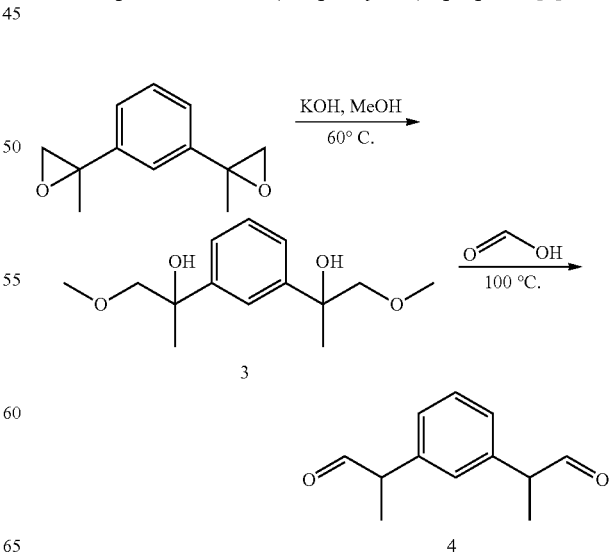

Dicarbinol 3 was prepared in a similar manner to di-carbinol 2 using procedure described in Method A. [LC-MS (Column B) tR: 4.55 min, 4.68 min (Exact mass: 254.15 m/z, found 254.2 m/z)]. Di-aldehyde 4 was prepared in a similar manner to di-aldehyde 2 using Method A.
GC-MS $t_R$: 14.22 min (Exact mass: 190.10 m/z, found: 190.1 m/z).

Method of Enol Ether Preparation:

Di-aldehyde was added to a nitrogen-swept, round-bottom flask fitted with overhead-stirrer, thermocouple, and Dean-Stark. Glycol alcohol solvent (5 equiv.) was added all at once, followed by the addition of toluene (2× mass of aldehyde used). Sodium methanesulfonate (0.025 equiv.) was added to the flask, followed by the addition of methanesulfonic acid (0.025 equiv.). The reaction was heated to reflux and held at that temperature for 15 hrs. Toluene was removed under reduced pressure using a rotary evaporator. Then 50% caustic (0.024 equiv.) was added all at once. The mixture was fractionally distilled under reduced pressure.

Example 1: Preparation of (E,E/Z,Z)-1,4-bis(1-(2-butoxyethoxy)prop-1-en-2-yl)benzene [5]

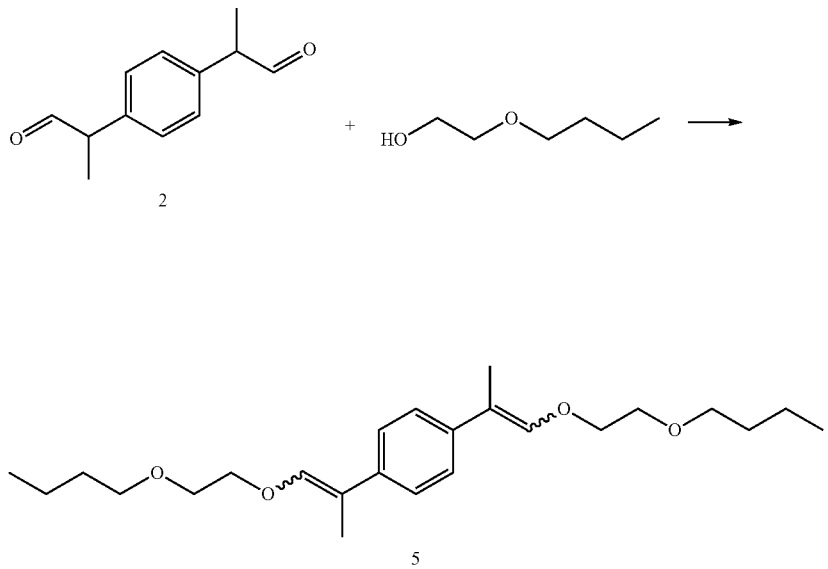

GC-MS $t_R$: 22.83 min, 24.34 min, 26.08 min (Exact mass: 390.28 m/z, found 390.3 m/z).

Example 2: Preparation of (E,E/Z,Z)-1,4-bis(1-((1-((1-methoxypropan-2-yl)oxy)propan-2-yl)oxy)prop-1-en-2-yl)benzene [6]

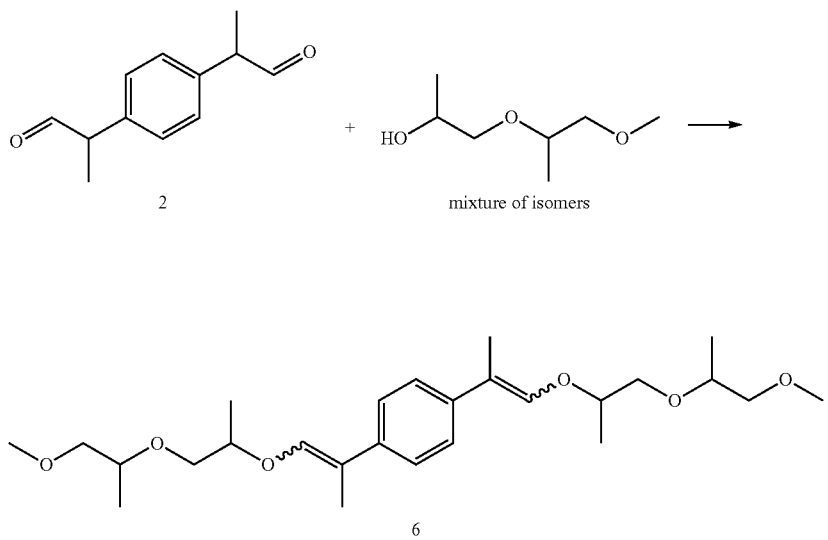

GC-MS $t_R$: 25.8 min, 26.2 min, 28.3 min, 28.9 min (Exact mass: 450.30 m/z, found 450 m/z).

Method B:

To a 4-necked round-bottom flask fitted with an overhead stirrer, thermocouple, and nitrogen inlet was added acetic anhydride (5 equiv.) and sodium bisulfate monohydrate (0.025 equiv.). The mixture was then heated to 65° C. and held for 30 minutes. The dicarbinol was then added dropwise over the course of 4-5 hrs via a pressure-equalizing addition funnel. Once the addition was complete, the reaction was checked by GC. Once complete, the mix was transferred to a 1-neck round-bottom flask and the excess acetic anhydride/acetic acid was removed under reduced pressure using a rotary evaporatory. The crude was taken up in toluene. The organics were then washed with 10% caustic (x2) solution and then 5% ammonium hydroxide solution. The mixture was dried with MgSO4 and simultaneously treated with activated carbon. After filtration, the volatiles were removed under reduced pressure using a rotary evaporator. Light-boiling impurities were removed by distillation. The enol ether/1,1-disubstituted olefin was Kugelrohr-distilled to afford product blends.

Example 3: A Mixture of (E,E/Z,Z)-1,4-bis(1-((1-((1-methoxypropan-2-yl)oxy)propan-2-yl)oxy)prop-1-en-2-yl)benzene [6a], (E,Z)-1-(1-((1-((1-methoxypropan-2-yl)oxy)propan-2-yl)oxy)prop-1-en-2-yl)-4-(3-((1-((1-methoxypropan-2-yl)oxy)propan-2-yl)oxy)prop-1-en-2-yl)benzene [6b], and 1,4-bis(3-((1-((1-methoxypropan-2-yl)oxy)propan-2-yl)oxy)prop-1-en-2-yl)benzene [6c]

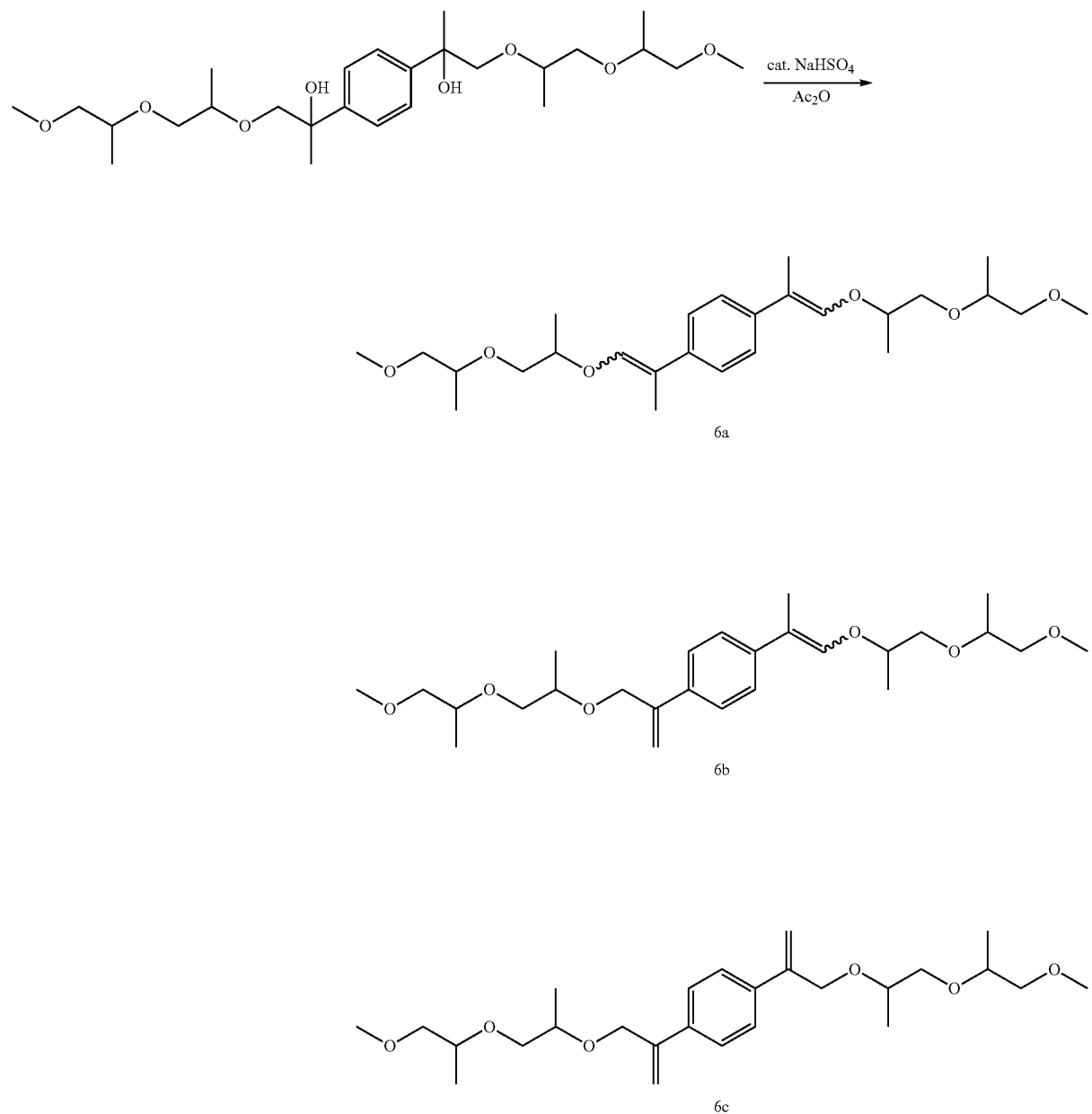

GC-MS $t_R$: 25.80 min, 26.28 min, 26.80 min, 27.30 min, 28.38 min, 28.94 min (Exact mass: 450.30 m/z, found: 450.4 m/z).

Example 4: A Mixture of (E,E/Z,Z)-1,4-bis(4,7,10-trimethyl-2,5,8,11-tetraoxatetradec-12-en-13-yl)benzene [7a], (E,Z)-4,7,10-trimethyl-13-(4-(4,7,10-trimethyl-2,5,8,11-tetraoxatetradec-13-en-13-yl)phenyl)-2,5,8,11-tetraoxatetradec-12-ene [7b], and 1,4-bis(4,7,10-trimethyl-2,5,8,11-tetraoxatetradec-13-en-13-yl)benzene [7c]

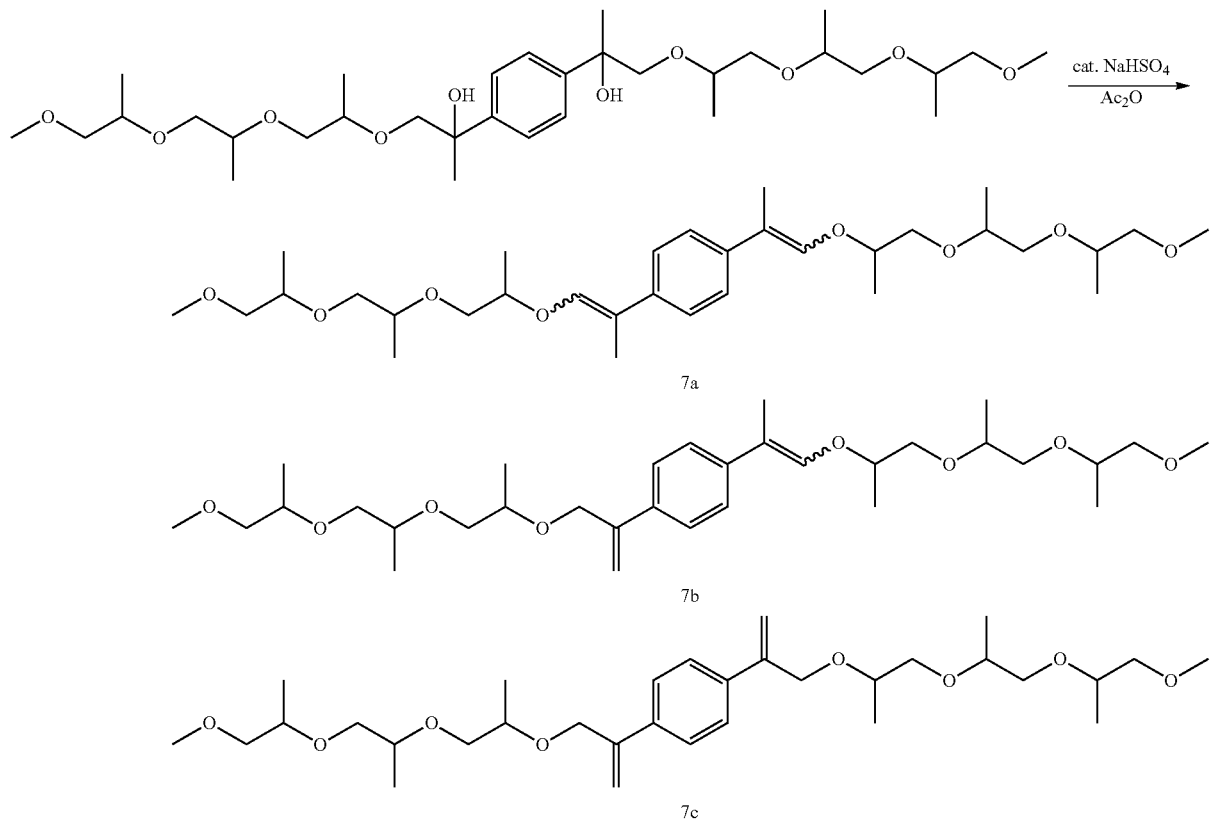

GC-MS $t_R$: 43.08 (broad peak), 69.53 min (broad peak) (Exact mass: 566.38 m/z, found: 566.5 m/z).

Example 5: A Mixture of (E,E/Z,Z)-1,4-bis(1-(2-(2-methoxyethoxy)ethoxy)prop-1-en-2-yl)benzene [8a], (E,Z)-1-(1-(2-(2-methoxyethoxy)ethoxy)prop-1-en-2-yl)-4-(3-(2-(2-methoxyethoxy)ethoxy)prop-1-en-2-yl)benzene [8b], and 1,4-bis(3-(2-(2-methoxyethoxy)ethoxy)prop-1-en-2-yl)benzene [8c]

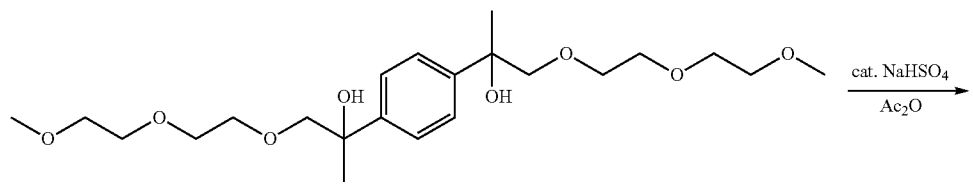

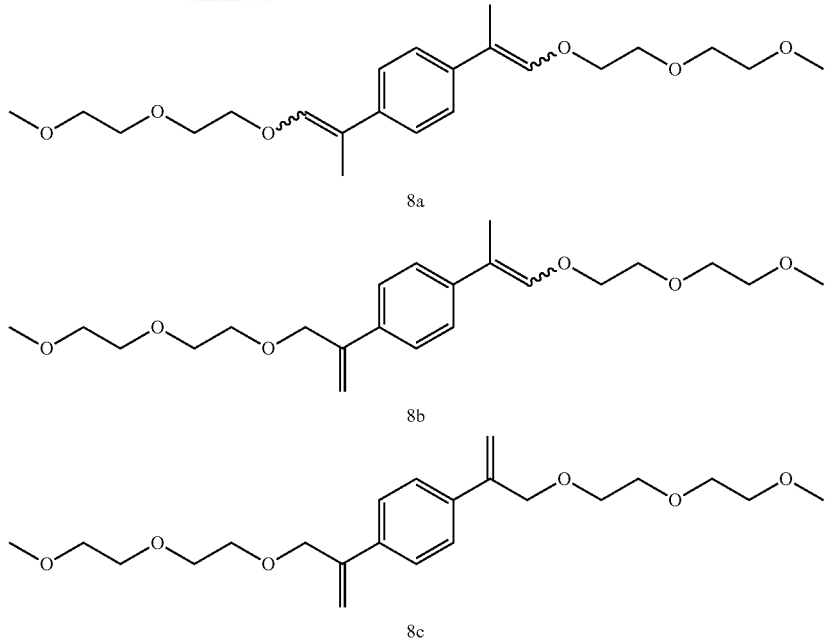
GC-MS $t_R$: 23.9 min, 24.29 min, 24.48 min, 25.64 min, 25.96 min, 27.63 min (Exact mass: 394.24 m/z, found: 394.3 m/z).
Example 6: a Mixture of (E,E/Z,Z)-1,4-bis(1-(2-(2-ethoxyethoxy)ethoxy)prop-1-en-2-yl)benzene [9a], (E/Z)-1-(1-(2-(2-ethoxyethoxy)ethoxy)prop-1-en-2-yl)-4-(3-(2-(2-ethoxyethoxy)ethoxy)prop-1-en-2-yl)benzene [9b], and 1,4-bis(3-(2-(2-ethoxyethoxy)ethoxy)prop-1-en-2-yl)benzene [9c]
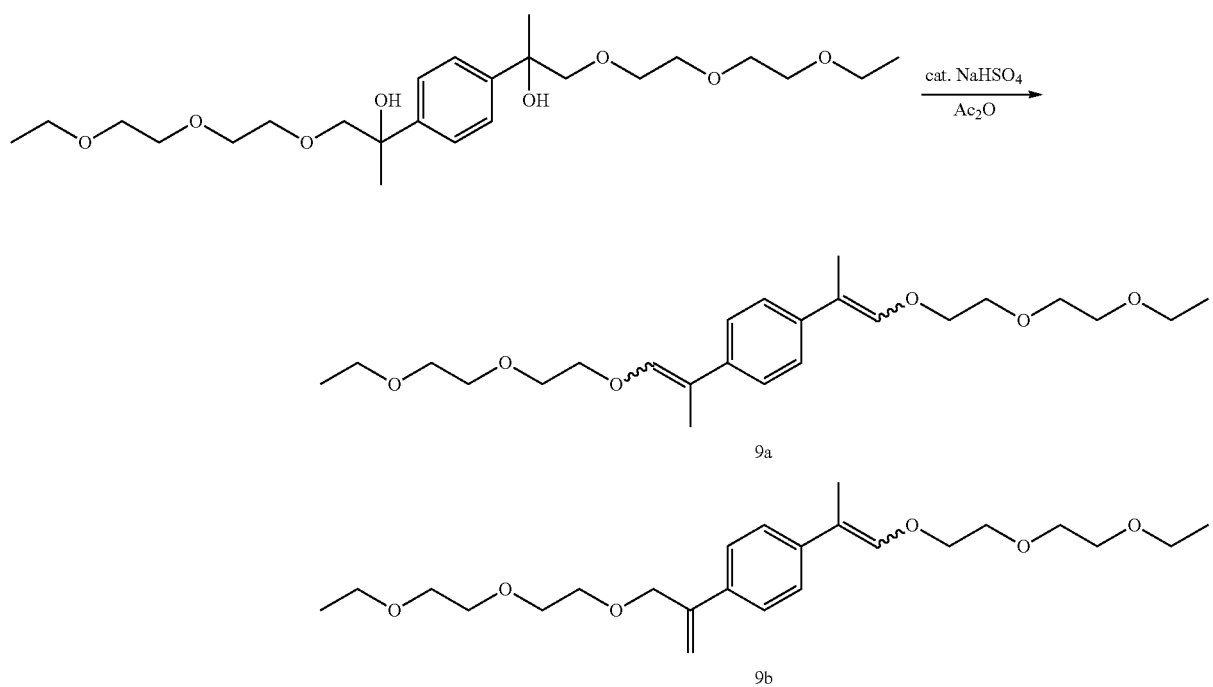

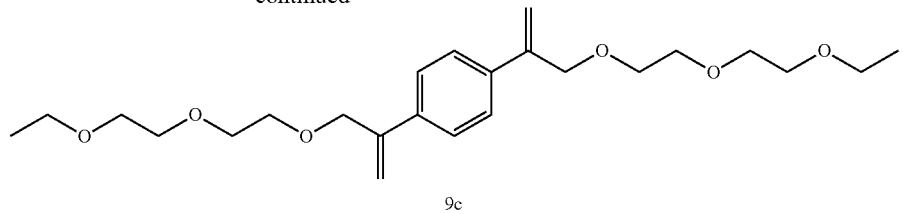
9c
GC-MS $t_R$: 25.64 min, 26.23 min, 26.55 min, 28.00 min, 28.47 min, 30.67 min (Exact mass: 422.27 m/z, found: 422.3 m/z).
Example 7: A Mixture of (E,E/Z,Z)-1,4-bis(1-(2-(2-propoxyethoxy)ethoxy)prop-1-en-2-yl)benzene [10a], (E,Z)-1-(1-(2-(2-propoxyethoxy)ethoxy)prop-1-en-2-yl)-4-(3-(2-(2-propoxyethoxy)ethoxy)prop-1-en-2-yl)benzene [10b], 1,4-bis(3-(2-(2-propoxyethoxy)ethoxy)prop-1-en-2-yl)benzene [10c]
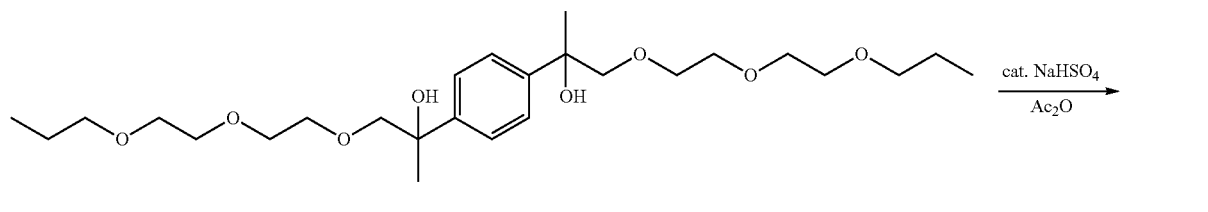
10a
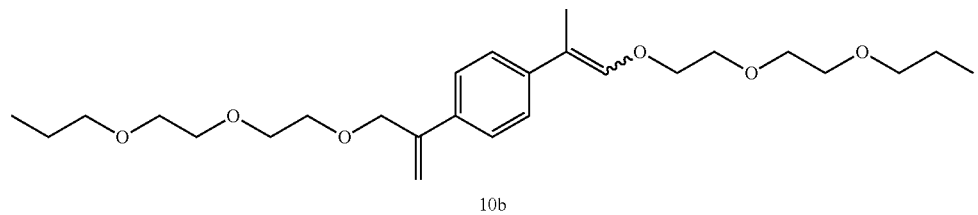
10b
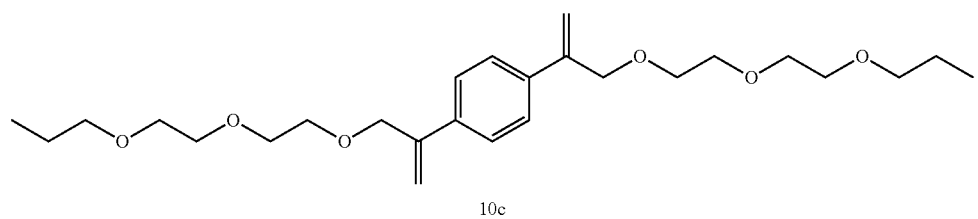
10c GC-MS $t_R$: 29.70 min, 30.67 min, 31.30 min, 33.27 min, 34.18 min, 37.58 min (Exact mass: 450.30 m/z, found: 450.3 m/z).

Example 8: A Mixture of (E,E/Z,Z)-1,4-bis(1-(2-(2-butoxyethoxy)ethoxy)prop-1-en-2-yl)benzene [11a], (E,Z)-1-(1-(2-(2-butoxyethoxy)ethoxy)prop-1-en-2-yl)-4-(3-(2-(2-butoxyethoxy)ethoxy)prop-1-en-2-yl)benzene [11b], 1,4-bis(3-(2-(2-butoxyethoxy)ethoxy)prop-1-en-2-yl)benzene [11c]

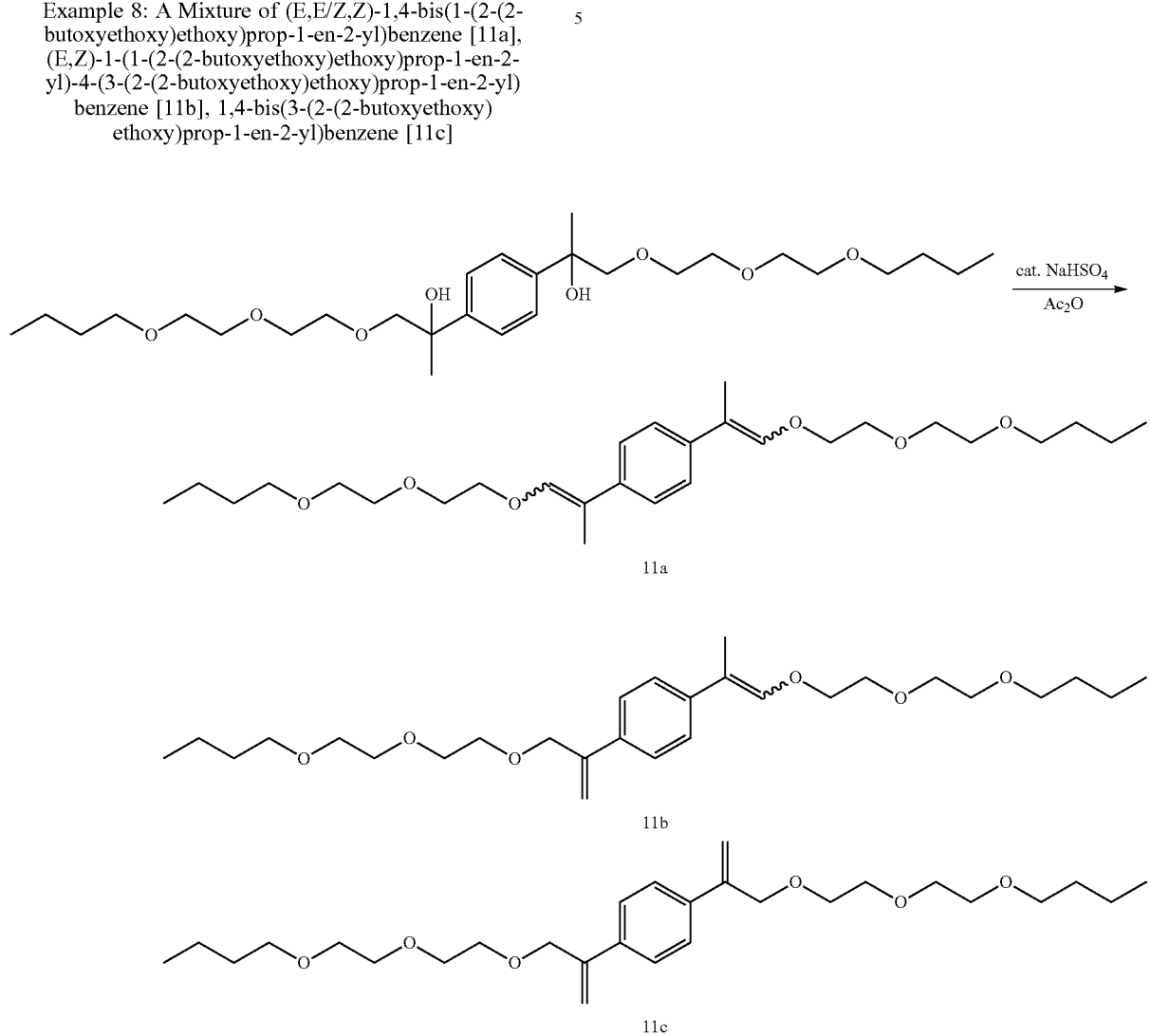

GC-MS $t_R$: 36.07 min, 37.71 min, 38.86 min, 41.45 min (Exact mass: 478.33 m/z, found: 478.4 m/z).

Example 9: A Mixture of (E,E/Z,Z)-1,4-di(2,5,8,11-tetraoxatetradec-12-en-13-yl)benzene [12a], (E,Z)-13-(4-(2,5,8,11-tetraoxatetradec-13-en-13-yl)phenyl)-2,5,8,11-tetraoxatetradec-12-ene [12b], and 1,4-di(2,5,8,11-tetraoxatetradec-13-en-13-yl)benzene [12c]

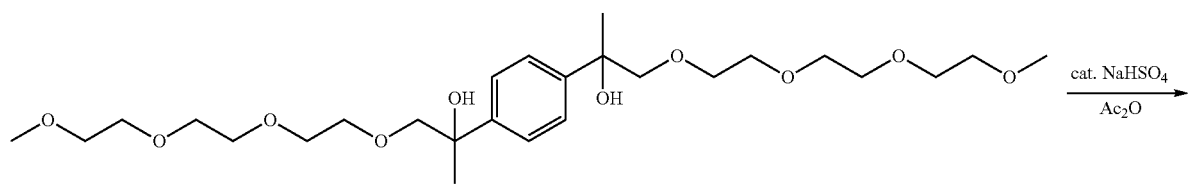

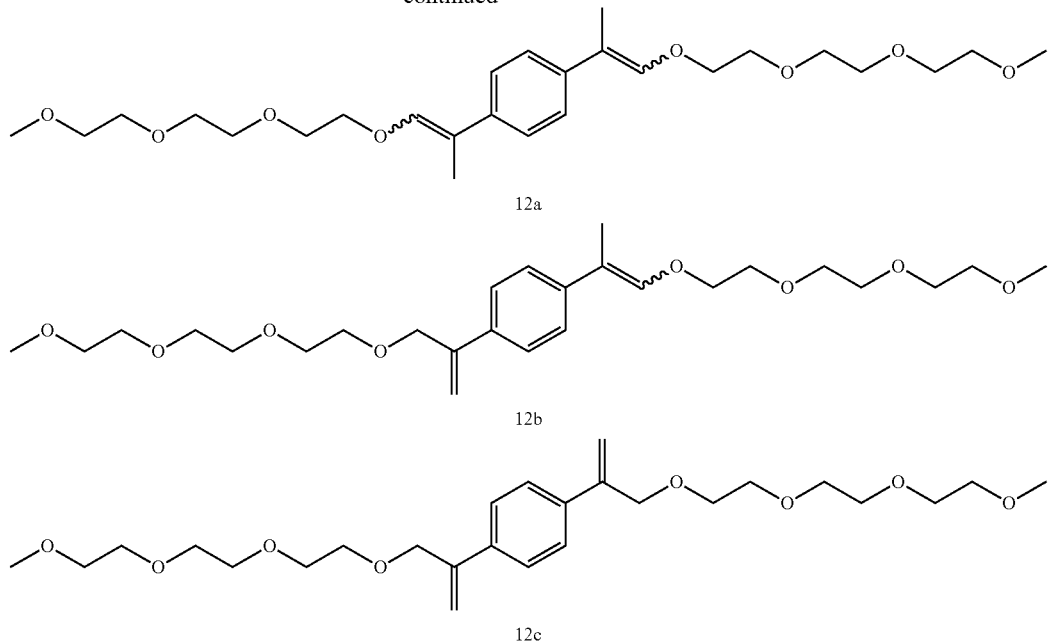
GC-MS $t_R$: 39.51 min, 41.51 min, 42.78 min, 46.43 min, 48.26 min, 55.04 min (Exact mass: 482.29 m/z, found: 482.4 m/z).
Example 10: A Mixture of (E,E/Z,Z)-1,3-bis(1-((1-((1-methoxypropan-2-yl)oxy)propan-2-yl)oxy)prop-1-en-2-yl)benzene [13a], (E/Z)-1-((1-((1-((1-methoxypropan-2-yl)oxy)propan-2-yl)oxy)prop-1-en-2-yl)-3-(3-((1-((1-methoxypropan-2-yl)oxy)propan-2-yl)oxy)prop-1-en-2-yl)benzene [13b], and 1,3-bis(3-((1-((1-methoxypropan-2-yl)oxy)propan-2-yl)oxy)prop-1-en-2-yl)benzene [13c]
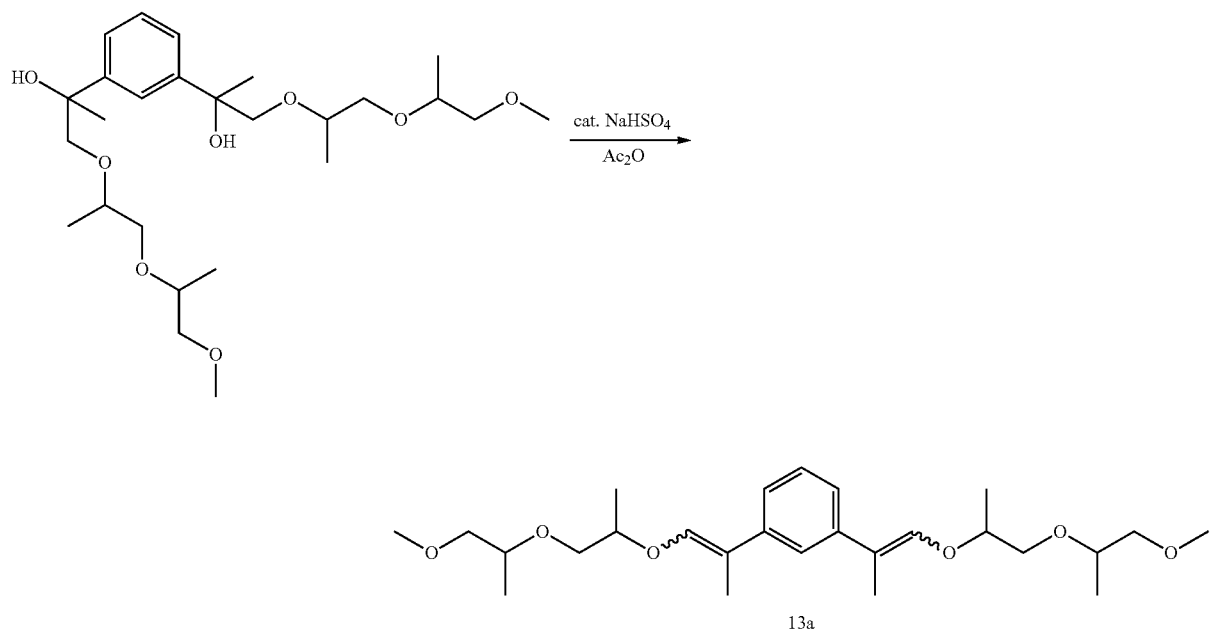

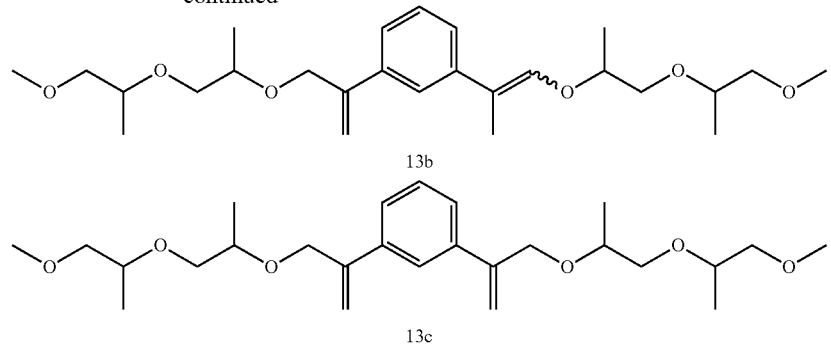
GC-MS $t_R$: 22.78 min, 23.14 min, 23.45 min, 23.91 min, 24.27 min, 24.59 min, 25.17 min, 25.58 min, 26.05 min (Exact mass: 450.30 m/z, found: 450.4 m/z).
Example 11: A Mixture of (E,E/Z,Z)-1,3-bis(4,7,10-trimethyl-2,5,8,11-tetraoxatetradec-12-en-13-yl)benzene [14a], (E/Z)-4,7,10-trimethyl-13-(3-(4,7,10-trimethyl-2,5,8,11-tetraoxatetradec-13-en-13-yl)phenyl)-2,5,8,11-tetraoxatetradec-12-ene [14b], and 1,3-bis(4,7,10-trimethyl-2,5,8,11-tetraoxatetradec-13-en-13-yl)benzene [14c]
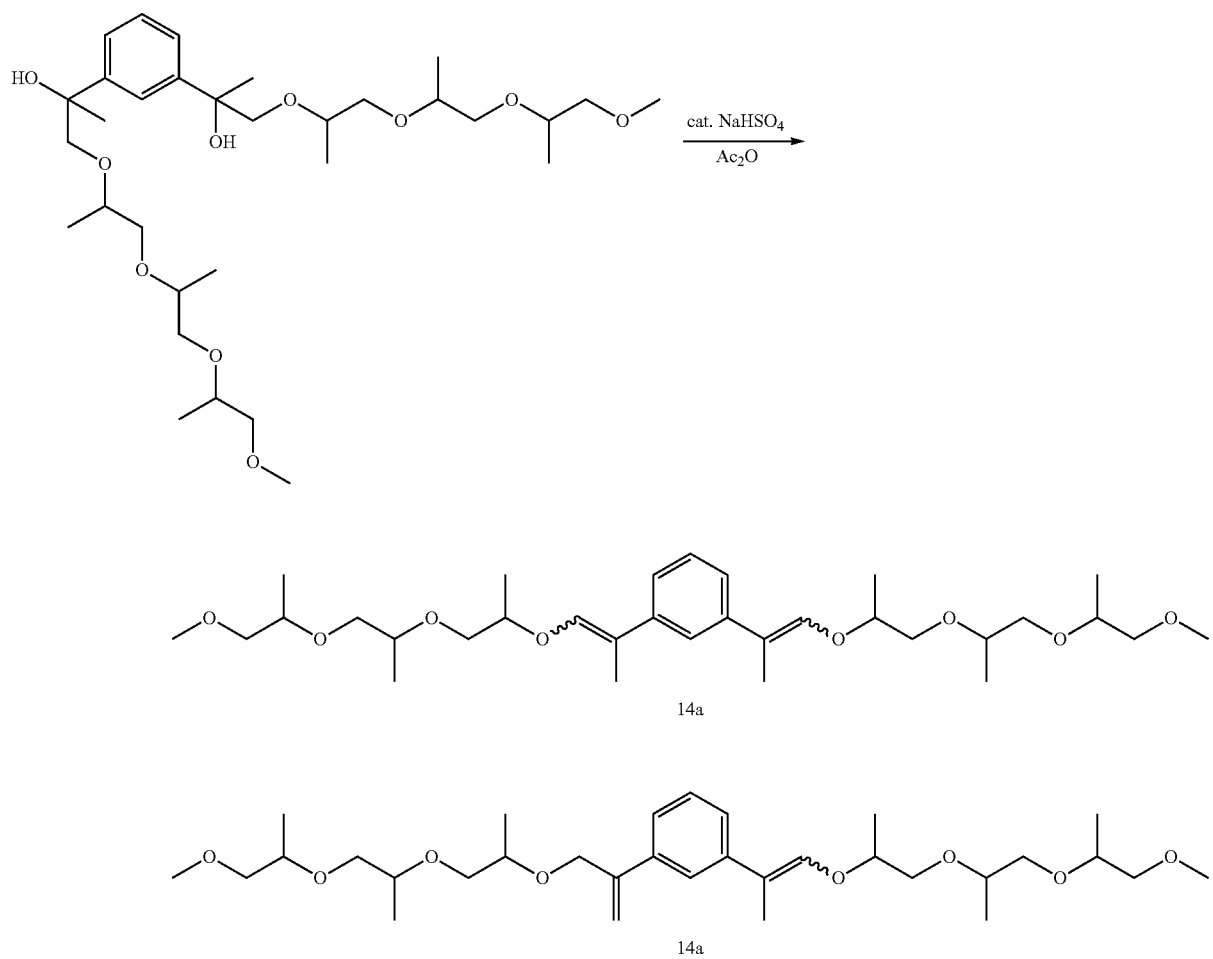

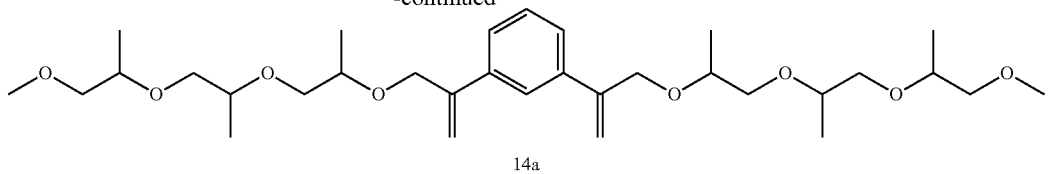
14a
GC-MS $t_R$: 41.84-43.72 min (broad peak) (Exact mass: 566.38 m/z, found: 566.5 m/z).
Example 12: A Mixture of (E,E/Z,Z)-1,3-bis(1-(2-(2-methoxyethoxy)ethoxy)prop-1-en-2-yl)benzene [15a], (E/Z)-1-(1-(2-(2-methoxyethoxy)ethoxy)prop-1-en-2-yl)-3-(3-(2-(2-methoxyethoxy)ethoxy)prop-1-en-2-yl)benzene [15b], 1,3-bis(3-(2-(2-methoxyethoxy)ethoxy)prop-1-en-2-yl)benzene [15c]
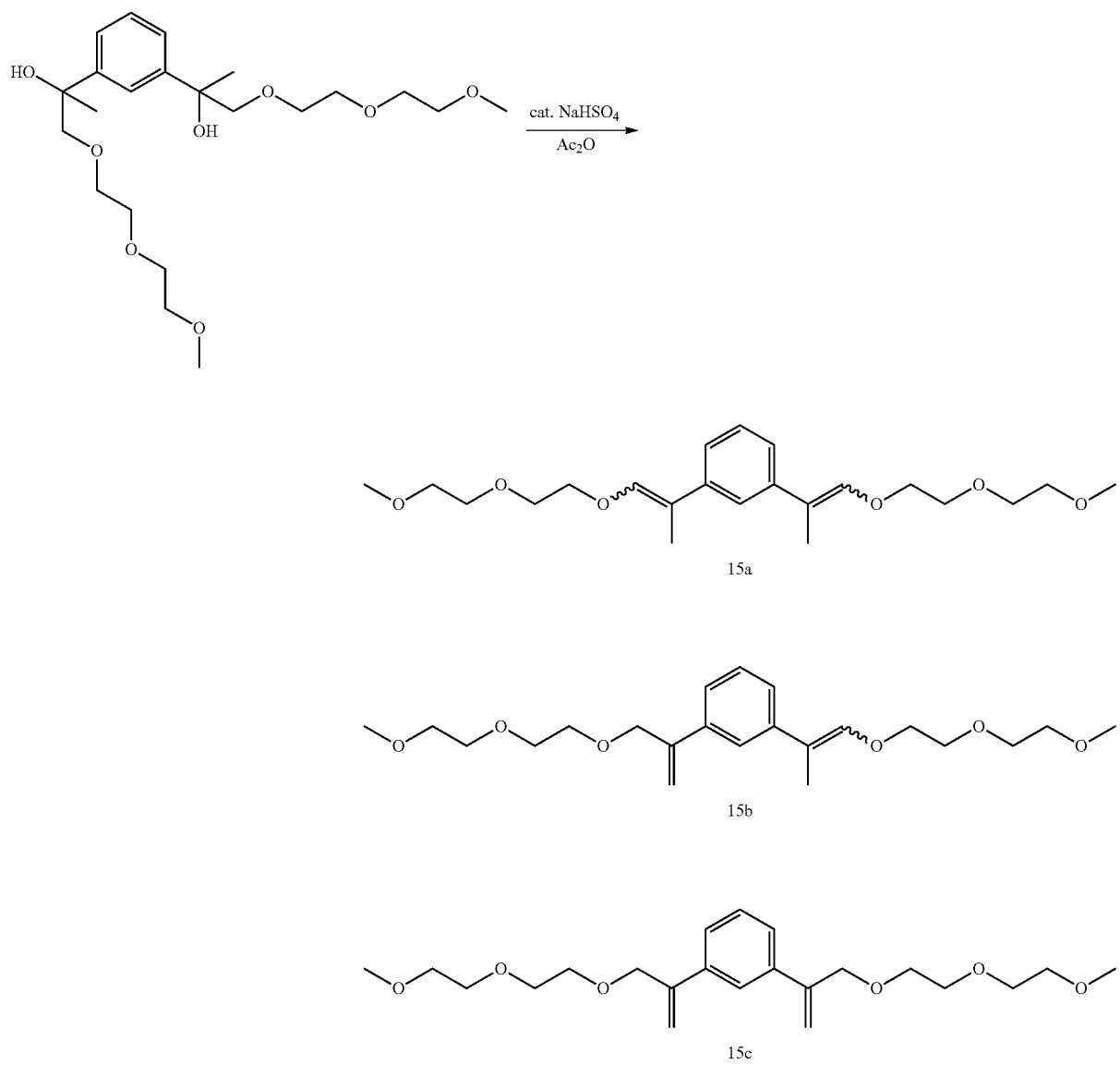

GC-MS $t_R$: 22.57 min, 22.91 min, 23.08 min, 23.79 min, 24.08 min, 25.43 min (Exact mass: 394.24 m/z, found: 394.3 m/z).

Example 13-1 and Example 13-2: A Mixture of (E,E/Z,Z)-1,3-bis(1-(2-(2-ethoxyethoxy)ethoxy)prop-1-en-2-yl)benzene [16a], (E/Z)-1-(1-(2-(2-ethoxyethoxy)ethoxy)prop-1-en-2-yl)-3-(3-(2-(2-ethoxyethoxy)ethoxy)prop-1-en-2-yl)benzene [16b], and 1,3-bis(3-(2-(2-ethoxyethoxy)ethoxy)prop-1-en-2-yl)benzene [16c]

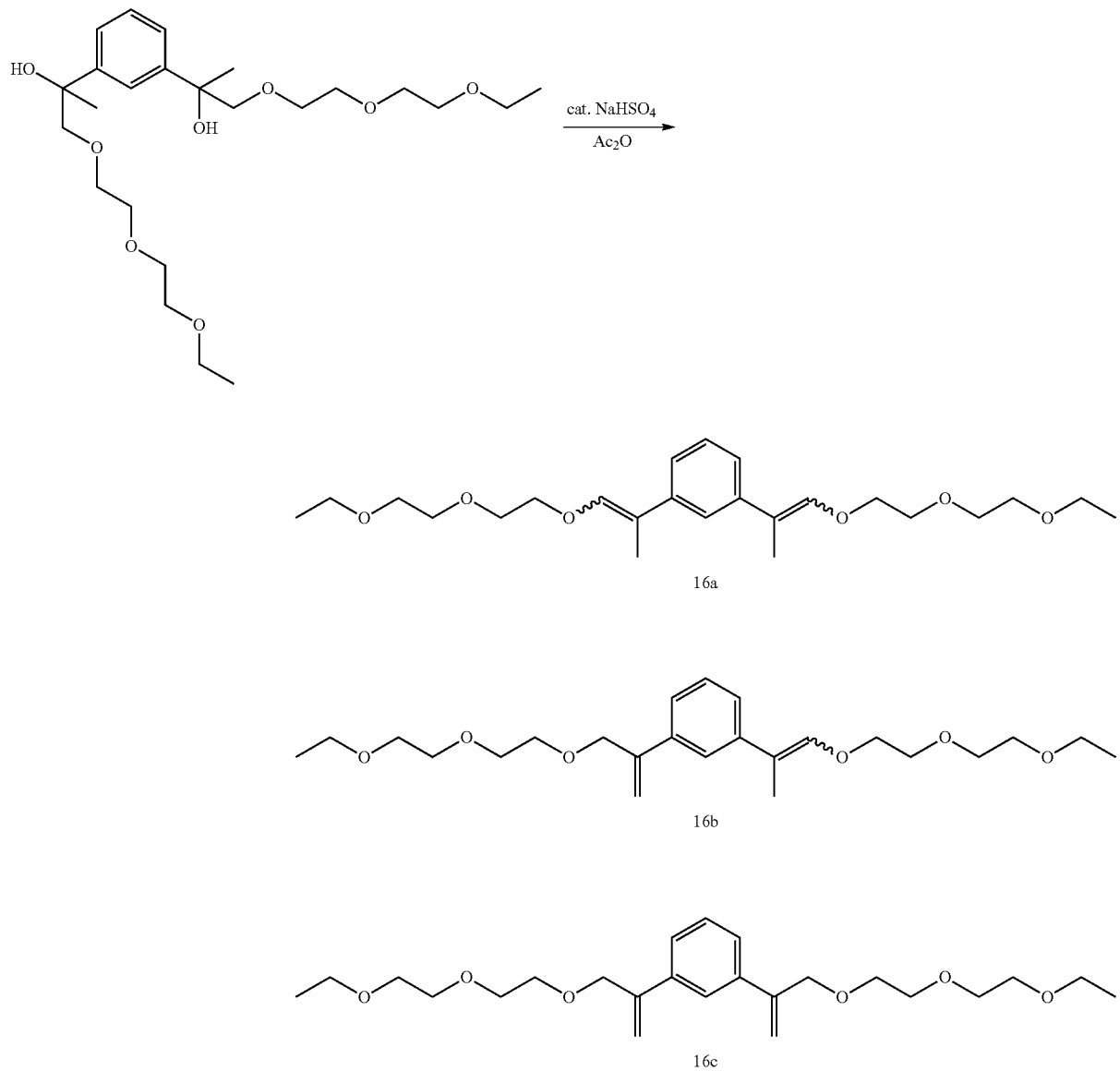

GC-MS $t_R$: 24.07 min, 24.73 min, 24.80 min, 25.72 min, 25.87 min, 27.78 min (Exact mass: 422.27 m/z, found: 422.3 m/z). 0.05 equiv. of sodium bisulfate used.

Example 13-1: 0.025 equiv. of sodium bisulfate used. Ratio of 16a:16b:16c=1.0:1.7:3.6

Example 13-2: 0.50 equiv. of sodium bisulfate used. Ratio of 16a:16b:16c=1.0:2.7:10

Example 14: A Mixture of (E,E/Z,Z)-1,3-bis(1-(2-(2-propoxyethoxy)ethoxy)prop-1-en-2-yl)benzene [17a], (E/Z)-1-(1-(2-(2-propoxyethoxy)ethoxy)prop-1-en-2-yl)-3-(3-(2-(2-propoxyethoxy)ethoxy)prop-1-en-2-yl)benzene [17b], and 1,3-bis(3-(2-(2-propoxyethoxy)ethoxy)prop-1-en-2-yl)benzene [17c]
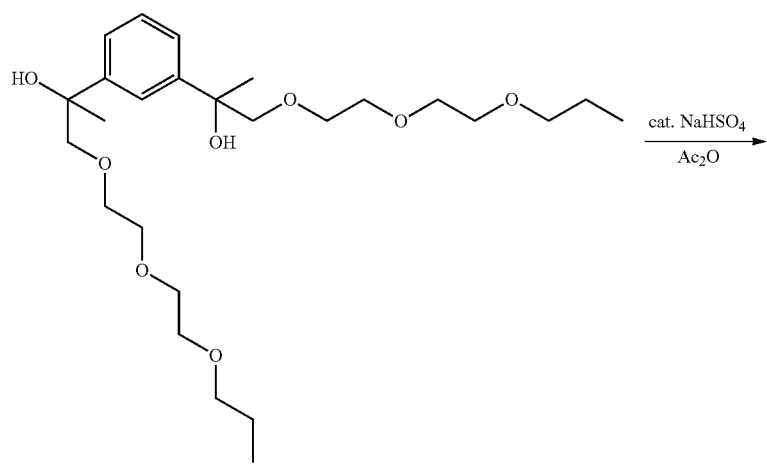
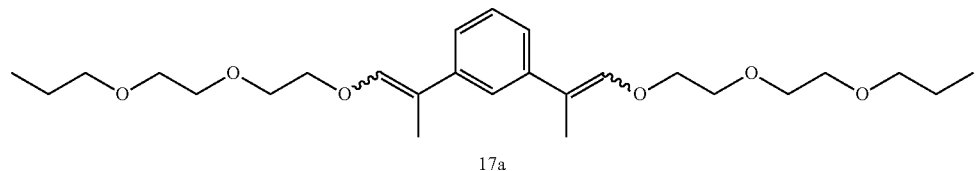
17a
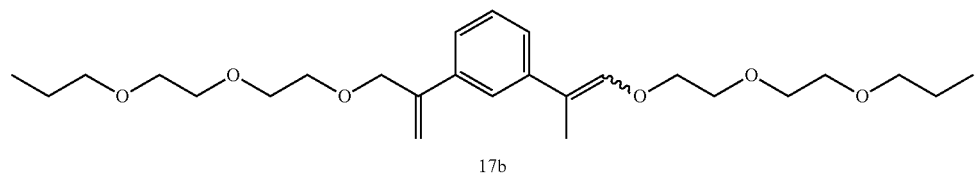
17b
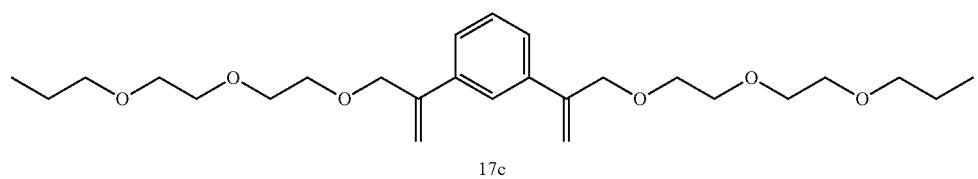
17c
GC-MS $t_R$: 27.42 min, 28.16 min, 28.63 min, 29.80 min, 30.61 min, 33.20 min (Exact mass: 450.30 m/z, found: 450.4 m/z).

Example 15: A Mixture of (E,E/Z,Z)-1,3-bis(1-(2-(2-butoxyethoxy)ethoxy)prop-1-en-2-yl)benzene [18a], (E/Z)-1-(1-(2-(2-butoxyethoxy)ethoxy)prop-1-en-2-yl)-3-(3-(2-(2-butoxyethoxy)ethoxy)prop-1-en-2-yl)benzene [18b], and 1,3-bis(3-(2-(2-butoxyethoxy)ethoxy)prop-1-en-2-yl)benzene [18c]
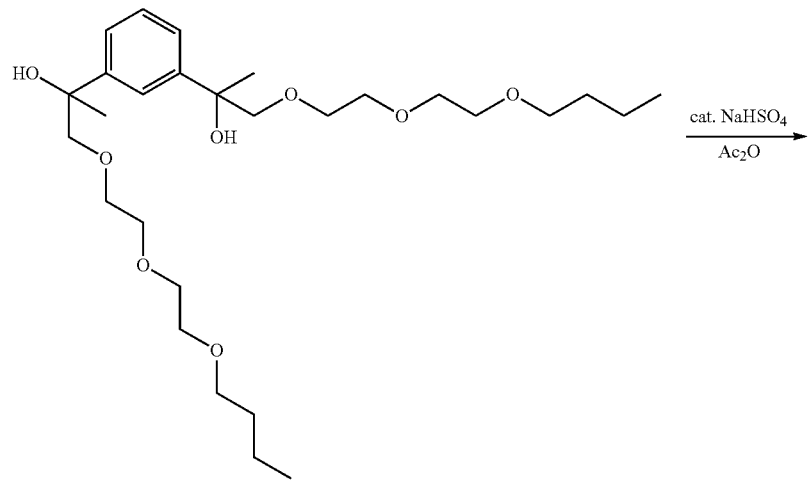
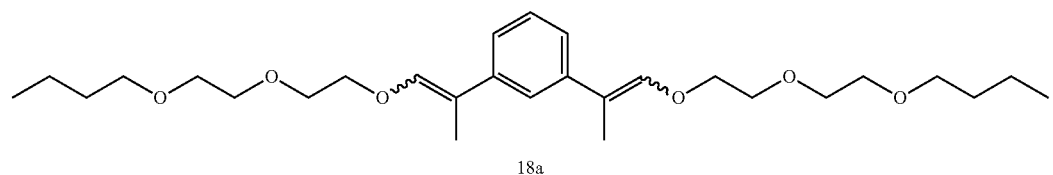
18a
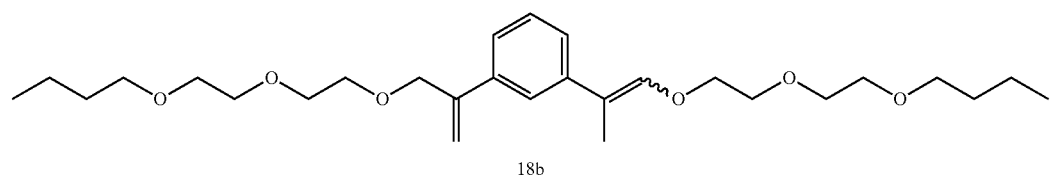
18b
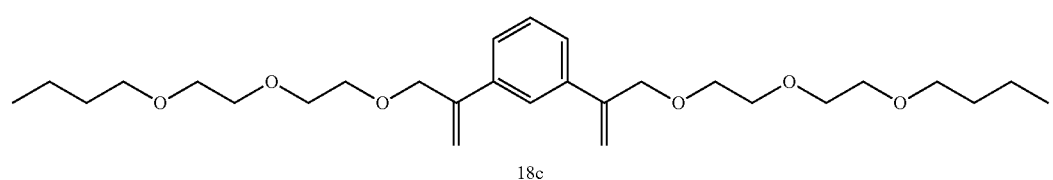
18c GC-MS $t_R$: 32.75 min, 33.89 min, 34.68 min, 36.20 min, 37.42 min, 41.29 min (Exact mass: 478.33 m/z, found: 478.4 m/z).
Example 16: A Mixture of (E,E/Z,Z)-1,3-di(2,5,8,11-tetraoxatetradec-12-en-13-yl)benzene [19a], (E/Z)-13-(3-(2,5,8,11-tetraoxatetradec-13-en-13-yl)phenyl)-2,5,8,11-tetraoxatetradec-12-ene [19b], and 1,3-di(2,5,8,11-tetraoxatetradec-13-en-13-yl)benzene [19c]
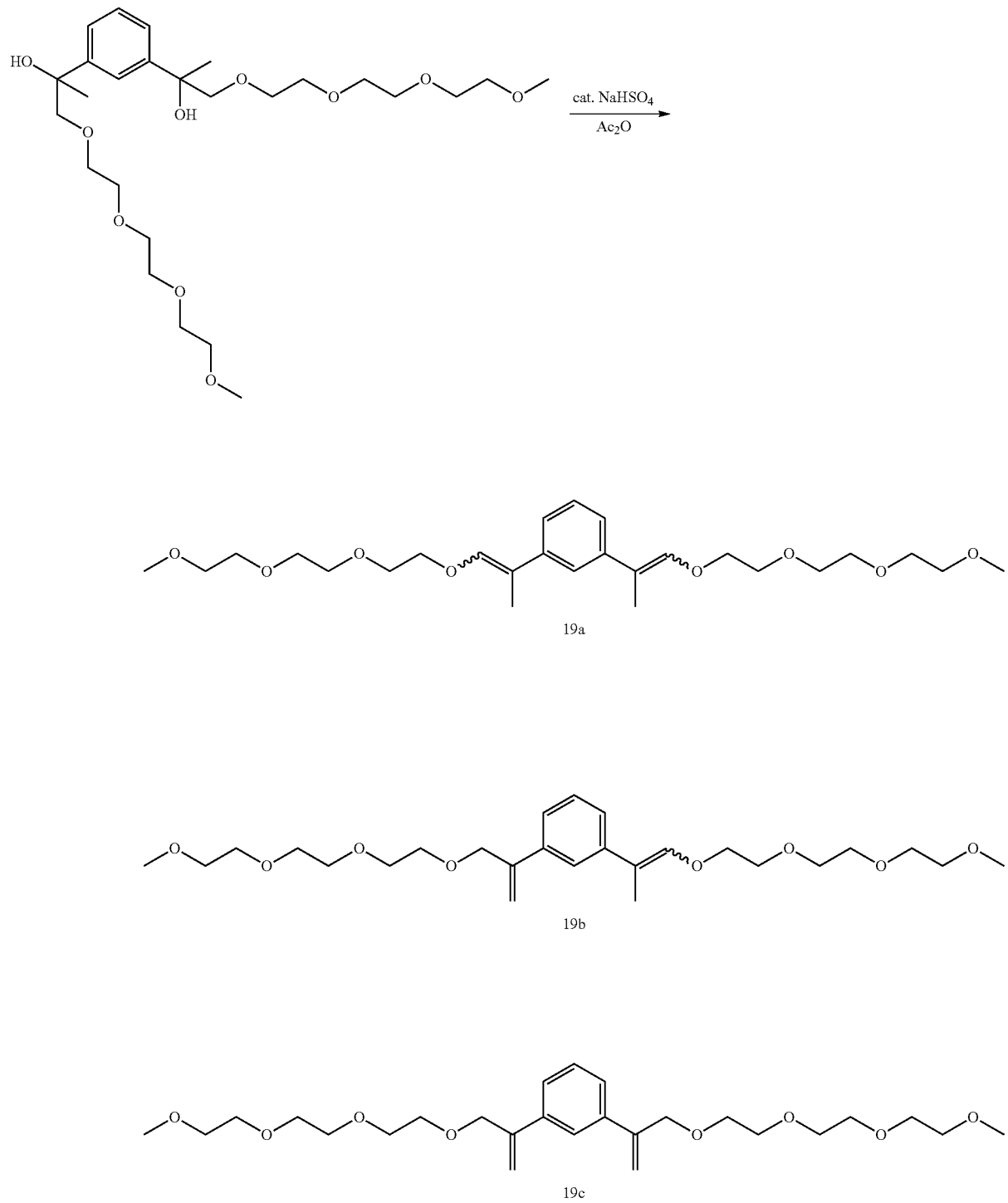

GC-MS $t_R$: 35.57 min, 36.92 min, 37.81 min, 39.66 min, 41.11 min, 45.59 min (Exact mass: 482.29 m/z, found: 482.3 m/z).

The examples described above were defined as non-VOC by ASTM D6886. This method uses MeP as a standard—if compound $t_R$>MeP $t_R$, compound is defined as non-VOC.
Conditions—Agilent 1100 LC
  Sample Prep: 2-3 mg/mL in DMSO
  Column A: Zorbax™ XDB-C18×4.6 mm, 5 μm
  Column B: Poroshell™ EC-C18 50×4.6 mm, 2.7 μm
  Column Temp: 40° C.
  Injection Volume: 2 μL
  DAD: 190-600 nm collection
  Pump Conditions: Initial—97% water (2.5 mM NH$_4$OAc) (Solvent A) and 3% acetonitrile (Solvent B)
  Gradient:

| Time (min) | % Solvent A | % Solvent B | Flow (mL/min) |
|---|---|---|---|
| 0 | 97 | 3 | 1.0 |
| 10 | 0 | 100 | 1.0 |
| 25 | 0 | 100 | 1.0 |
| 25.1 | 97 | 3 | 1.0 |
| 30 | 97 | 3 | 1.0 |

Mass spectra were acquired with a Micromass LCT mass spectrometer, which was coupled to the LC. Mass spectra were collected using electrospray ionization in both the positive-ion and negative ion modes. Ammonium acetate (50 mM in MeOH) was added post column (0.1 mL/min) to enhance ionization efficiency. ES+/ES− scan range was 60-3300 amu (25 and 75V).
GC-MS Instrument Parameters—Agilent 6890N GC with Agilent 5975B VL MSD
  Sample Prep: 100 μL sample diluted to 1 mL with toluene; Column: DB-5 30 m×0.25 mm×0.25 μm; Oven Ramp: 0-4.5 mins at 40° C.; Ramp 20 C/min to 280 C, Hold 53.5 mins; Injector: Temperature—250° C.; Split Flow—65 mL/min; Carrier Flow Rate—1.3 mL/min; Volume—1.0 μL; MS: Transfer Line—280° C.; Ion Source Temp—230° C.; Mass Range—34-700 amu. Methyl palmitate $t_R$=16.6 min using the above method.

Minimum Film-Forming Temperature (MFFT) Screening: ASTM 02354-10e

MFFT efficiency testing was based on ASTM D2354. The model instrument used was an MFFT-90 bar which allows samples to be tested from −10° C. to 90° C. For waterborne latexes, reaching a temperature of 2° C. is the primary goal. To reach that temperature, the MFFT bar was set to range from 0° C. to 18° C. This range is important since those Tg values for waterborne latexes somewhat correlate with their coinciding MFFT value. The higher the Tg value, the higher the MFFT value and vice versa. Neat commercial architectural latexes typically lie within this temperature range when testing for MFFT efficiency. Depending on the Tg of the material being tested, the range can be adjusted accordingly to determine the film's MFFT.

The ultimate goal for the final paint is to form a continuous film at a low temperature (2° C.). To achieve this, the MFFT of the neat latex material is first determined. If the neat latex material is above an MFFT of 2° C., we will add reactive film-hardening additive at different phr (% additive based on latex solids) levels to allow the latex to reach 2° C. To reach that temperature, a linear regression of the phr levels is performed. This allows one to determine the appropriate amount of reactive film-hardening additive to add to the final paint formulation. In addition to the determined phr values from the MFFT screening, one additional phr is added to the final paint formulation to account for pigmentation.

Test Procedure:
1. Turn water source, MFFT instrument, and nitrogen source on in that order
2. Let MFFT instrument equilibrate ~15 minutes
3. Raise lid on the instrument and place the film caster (~6 WFT) at the cold end (0°) of the bar
4. Our film caster is sectioned into individual squares allowing us to test up to five latex samples at a time
5. Add samples to film caster
6. Draw down samples from cold end to the warm end (18° C.) of the MFFT bar
7. Lower the lid on the instrument
8. Samples will be ready to evaluate in approximately 1-2 hours

TABLE 2

| | Latex | | | | | | | |
|---|---|---|---|---|---|---|---|---|
| | Rhoplex™ SG-30 | | Acronal™ 296 D | | Encor™ 379 | | Rhoplex™ HG-95 | |
| Ex # | 4.0° C. (phr) | 2.0° C. (phr) | 4.0° C. (phr) | 2.0° C. (phr) | 4.0° C. (phr) | 2.0° C. (phr) | 4.0° C. (phr) | 2.0° C. (phr) |
| Texanol™ | 4.62 | 5.45 | 6.78 | 7.80 | 2.91 | 4.13 | 9.38 | 10.38 |
| OE400 | 4.82 | 5.66 | 6.51 | 7.53 | 3.04 | 4.33 | 11.38 | 12.56 |
| Citroflex™ 4 | 4.47 | 5.25 | 5.63 | 6.49 | 3.14 | 4.51 | 10.70 | 11.81 |
| Example 6 | 5.51 | 6.54 | 6.40 | 7.42 | 3.66 | 5.17 | 12.20 | 13.46 |
| Example 10 | 6.77 | 8.01 | 7.38 | 8.52 | 4.13 | 5.91 | 16.37 | 18.08 |
| Example 13-1 | 5.45 | 6.46 | 6.74 | 7.75 | 2.97 | 4.26 | 12.01 | 13.25 |
| Example 13-2 | 5.54 | 6.58 | 5.78 | 6.65 | 3.62 | 5.15 | 12.71 | 14.03 |
| Example 14 | 4.63 | 5.45 | 5.50 | 6.34 | 3.39 | 4.82 | 12.22 | 13.49 |

Parts per hundred resin (PHR) of Texanol™, OE400, Citroflex™ 4, or reactive film-hardening additive required to lower MFFT to 4.0° C. and 2.0° C. in Rhoplex™ SG-30, Acronal™ 296 D, Encor™ 379, and Rhoplex™ HG-95 model coating systems.

9. New MFFT bar instruments are equipped with a cursor. Moving the cursor to the MFFT point of a sample, the temperature value will be shown on a digital display

TABLE 3

Common Grind formulation: Rhoplex™ SG-30

| Component | Weight (g) |
|---|---|
| Water | 1230.00 |
| NATROSOL™ PLUS 330 | 12.30 |
| (Mix 5 Minutes) | |
| TAMOL™ 165A | 55.76 |
| Triton™ CF-10 | 16.40 |
| AMP-95 | 16.40 |
| BYK-024 | 20.50 |
| TRONOX® 826S | 2885.58 |
| KATHON™ LX 1.5% | 14.76 |
| (Mix 15 Minutes) | |
| Total: | 4251.70 |

TABLE 4

Master Paint Formulations. Rhoplex™ SG-30

| | Formulation A | Formulation B | Formulation C | Formulation D |
|---|---|---|---|---|
| Common Grind (g) | 518.50 | 518.50 | 518.50 | 518.50 |
| Rhoplex™ SG-30 (g) | 450.30 | 450.30 | 450.30 | 450.30 |
| Coalescent (g) | Texanol™ (14.86) | OE400 (15.00) | Citroflex™ 4 (13.96) | 0 |
| RFHA (g) | 0 | 0 | 0 | Ex 6 (16.89) |
| Acrysol™ RM-6000 (g) (Mix 10 Minutes) | 20.00 | 20.00 | 20.00 | 20.00 |
| Water (g) | 57.36 | 57.50 | 59.61 | 56.48 |
| Acrysol™ RM-725 (g) (Final Mix 15 Minutes) | 1.75 | 1.75 | 1.75 | 1.75 |
| Total (g) | 1062.77 | 1063.05 | 1064.12 | 1063.91 |

| | Formulation E | Formulation F | Formulation G | Formulation H |
|---|---|---|---|---|
| Common Grind (g) | 518.50 | 518.50 | 518.50 | 518.50 |
| Rhoplex™ SG-30 (g) | 450.30 | 450.30 | 450.30 | 450.30 |
| Coalescent (g) | 0 | 0 | 0 | 0 |
| RFHA (g) | Ex 10 (20.26) | Ex 13-1 (16.89) | Ex 13-2 (17.11) | Ex 14 (14.41) |
| Acrysol™ RM-6000 (g) (Mix 10 Minutes) | 20.00 | 20.00 | 20.00 | 20.00 |
| Water (g) | 53.47 | 56.78 | 56.59 | 58.90 |
| Acrysol™ RM-725 (g) (Final Mix 15 Minutes) | 1.75 | 1.75 | 1.75 | 1.75 |
| Total (g) | 1064.28 | 1064.22 | 1064.25 | 1063.86 |

TABLE 5

Stability of wet paint formulations: Rhoplex™ SG-30

| | Initial | | | 24 hr | | | | 1 Week | | | |
|---|---|---|---|---|---|---|---|---|---|---|---|
| Formulation | KU | pH | ICI (poise) | KU | Δ KU | ICI (poise) | pH | KU | Δ KU | ICI (poise) | pH |
| A | 95.6 | 9.38 | 1.064 | 100.8 | 5.2 | 1.073 | 9.41 | 103.2 | 7.6 | 1.144 | 9.37 |
| B | 95.6 | 9.37 | 1.041 | 100.6 | 5.0 | 1.108 | 9.42 | 103.7 | 8.1 | 1.158 | 9.40 |
| C | 95.1 | 9.37 | 0.989 | 99.8 | 4.7 | 1.031 | 9.43 | 103.0 | 7.9 | 1.116 | 9.39 |
| D | 95.8 | 9.40 | 1.036 | 101.1 | 5.3 | 1.228 | 9.37 | 103.5 | 7.7 | 1.186 | 9.29 |
| E | 97.4 | 9.34 | 1.144 | 101.0 | 3.6 | 1.111 | 9.40 | 103.2 | 5.8 | 1.209 | 9.44 |
| F | 95.7 | 9.42 | 0.989 | 97.8 | 2.1 | 1.050 | 9.42 | 101.4 | 5.7 | 1.163 | 9.39 |
| G | 98.3 | 9.27 | 1.041 | 103.1 | 4.8 | 1.125 | 9.39 | 105.0 | 6.7 | 1.256 | 9.37 |
| H | 95.2 | 9.42 | 1.078 | 97.6 | 2.4 | 1.228 | 9.39 | 101.3 | 6.1 | 1.116 | 9.43 |

Stormer viscosities were measured with a KU-2 viscometer by Brookfield. ICI viscosities were measured with a BYK CAP 2000 + viscometer.

TABLE 6

28-day König hardness: Rhoplex™ SG-30

| Formulation | Dry Time (1 Day) Hardness (sec) | Dry Time (7 Days) Hardness (sec) | Dry Time (14 Days) Hardness (sec) | Dry Time (21 Days) Hardness (sec) | Dry Time (28 Days) Hardness (sec) |
|---|---|---|---|---|---|
| A | 15 | 19 | 24 | 24 | 25 |
| B | 10 | 10 | 10 | 11 | 11 |
| C | 13 | 12 | 13 | 13 | 12 |
| D | 13 | 18 | 21 | 21 | 22 |
| E | 13 | 14 | 16 | 18 | 18 |
| F | 11 | 15 | 19 | 20 | 21 |
| G | 12 | 16 | 17 | 20 | 20 |
| H | 13 | 17 | 21 | 21 | 20 |

Drawdowns of the paints (3 mil wet on aluminum panels) were prepared for König testing. All drawdowns were stored in a controlled temperature room until use. König testing was done using BYK Gardner pendulum hardness tester. Reported values are the average of three measurements per panel.

TABLE 7

14-day block resistance: Rhoplex™ SG-30

| Formulation | Dry Time (1 Day) Block Resistance | Dry Time (7 Days) Block Resistance | Dry Time (14 Days) Block Resistance |
|---|---|---|---|
| A | 6 | 8 | 9 |
| B | 5 | 6 | 7 |
| C | 5 | 6 | 8 |
| D | 6 | 10 | 10 |
| E | 6 | 9 | 10 |
| F | 6 | 9 | 10 |
| G | 6 | 9 | 10 |
| H | 6 | 10 | 10 |

Drawdowns of the paints (6 mil wet on Form BH Leneta charts) were prepared for Block Resistance testing. All drawdowns were stored in a controlled temperature room until use. Testing was done based on ASTM method D4946. Reported values are the average of three measurements per panel.

TABLE 8

Common Grind formulation: Acronal™ 296D

| Component | Weight (g) |
|---|---|
| Water | 1230.00 |
| NATROSOL™ PLUS 330 (Mix 5 Minutes) | 12.30 |
| TAMOL™ 165A | 55.76 |
| Triton™ CF-10 | 16.40 |
| AMP-95 | 16.40 |
| BYK-024 | 20.50 |
| TRONOX® 826S | 2885.58 |
| KATHON™ LX 1.5% (Mix 15 Minutes) | 14.76 |
| Total: | 4251.70 |

TABLE 9

Master Paint Formulations: Acronal™ 296D

| | Formulation A | Formulation B | Formulation C | Formulation D | Formulation E | Formulation F | Formulation G | Formulation H |
|---|---|---|---|---|---|---|---|---|
| Common Grind (g) | 518.50 | 518.50 | 518.50 | 518.50 | 518.50 | 518.50 | 518.50 | 518.50 |
| Acronal™ 296D (g) | 432.00 | 432.00 | 432.00 | 432.00 | 676.0 | 451.2 | 450.5 | 450.2 |
| Coalescent (g) | Texanol™ (19.01) | OE400 (18.36) | Citroflex™ 4 (16.20) | 0 | 0 | 0 | 0 | 0 |
| RFHA (g) | 0 | 0 | 0 | Ex 6 (18.14) | Ex 10 (20.52) | Ex 13-1 (18.79) | Ex 13-2 (16.42) | Ex 14 (15.77) |
| Acrysol™ RM-6000 (g) (Mix 10 Minutes) | 20.00 | 20.00 | 20.00 | 20.00 | 20.00 | 20.00 | 20.00 | 20.00 |
| Water (g) | 59.70 | 60.74 | 64.17 | 61.96 | 59.93 | 61.66 | 63.96 | 64.28 |
| Acrysol™ RM-725 (g) (Final Mix 15 Minutes) | 3.40 | 3.40 | 3.40 | 3.40 | 3.40 | 3.40 | 3.40 | 3.40 |
| Total (g) | 1052.61 | 1053.00 | 1054.27 | 1054.00 | 1054.35 | 1054.35 | 1054.28 | 1053.95 |

TABLE 10

Stability of wet paint formulations: Acronal™ 296D

| | Initial | | | 24 hr | | | | 1 Week | | | |
|---|---|---|---|---|---|---|---|---|---|---|---|
| Formulation | KU | pH | ICI (poise) | KU | Δ KU | ICI (poise) | pH | KU | Δ KU | ICI (poise) | pH |
| A | 96.3 | 9.05 | 1.383 | 104.2 | 7.9 | 1.355 | 9.08 | 107.2 | 10.9 | 1.383 | 8.92 |
| B | 94.6 | 9.10 | 1.242 | 103.0 | 8.4 | 1.200 | 9.06 | 105.3 | 10.7 | 1.242 | 9.03 |
| C | 94.0 | 9.07 | 1.284 | 101.6 | 7.6 | 1.219 | 9.03 | 104.3 | 10.3 | 1.341 | 8.94 |

TABLE 10-continued

Stability of wet paint formulations: Acronal™ 296D

| | Initial | | | 24 hr | | | | 1 Week | | | |
|---|---|---|---|---|---|---|---|---|---|---|---|
| Formulation | KU | pH | ICI (poise) | KU | Δ KU | ICI (poise) | pH | KU | Δ KU | ICI (poise) | pH |
| D | 95.0 | 9.05 | 1.256 | 103.0 | 8.0 | 1.303 | 9.05 | 105.4 | 10.4 | 1.280 | 8.92 |
| E | 97.5 | 9.05 | 1.298 | 104.9 | 7.4 | 1.252 | 9.05 | 107.6 | 10.1 | 1.298 | 8.94 |
| F | 93.4 | 9.06 | 1.214 | 101.4 | 8.0 | 1.181 | 9.09 | 104.2 | 10.8 | 1.303 | 9.05 |
| G | 93.5 | 9.00 | 1.223 | 100.7 | 7.2 | 1.181 | 9.10 | 100.8 | 7.3 | 1.327 | 8.91 |
| H | 94.0 | 9.05 | 1.167 | 102.0 | 8.0 | 1.228 | 9.11 | 104.7 | 10.7 | 1.167 | 9.04 |

Stormer viscosities were measured with a KU-2 viscometer by Brookfield. ICI viscosities were measured with a BYK CAP 2000 + viscometer.

TABLE 11

28-day König hardness: Acronal™ 296D

| Formulation | Dry Time (1 Day) Hardness (sec) | Dry Time (7 Days) Hardness (sec) | Dry Time (14 Days) Hardness (sec) | Dry Time (21 Days) Hardness (sec) | Dry Time (28 Days) Hardness (sec) |
|---|---|---|---|---|---|
| A | 11 | 16 | 20 | 23 | 22 |
| B | 7 | 8 | 8 | 8 | 8 |
| C | 6 | 7 | 7 | 8 | 8 |
| D | 7 | 14 | 16 | 17 | 16 |
| E | 8 | 13 | 15 | 15 | 15 |
| F | 7 | 11 | 13 | 15 | 14 |
| G | 8 | 14 | 15 | 17 | 17 |
| H | 7 | 12 | 15 | 16 | 15 |

Drawdowns of the paints (3 mil wet on aluminum panels) were prepared for König testing. All drawdowns were stored in a controlled temperature room until use. König testing was done using BYK Gardner pendulum hardness tester. Reported values are the average of three measurements per panel.

TABLE 12

14-day block resistance: Acronal™ 296D

| Formulation | Dry Time (1 Day) Block Resistance | Dry Time (7 Days) Block Resistance | Dry Time (14 Days) Block Resistance |
|---|---|---|---|
| A | 0 | 1 | 3 |
| B | 0 | 0 | 0 |
| C | 0 | 0 | 0 |
| D | 4 | 7 | 8 |
| E | 4 | 7 | 8 |
| F | 4 | 7 | 7 |
| G | 4 | 8 | 8 |
| H | 4 | 8 | 8 |

Drawdowns of the paints (6 mil wet on Form BH Leneta charts) were prepared for Block Resistance testing. All drawdowns were stored in a controlled temperature room until use. Testing was done based on ASTM method D4946. Reported values are the average of three measurements per panel.

TABLE 13

Common Grind formulation: Encor™ 379G

| Component | Weight (g) |
|---|---|
| Water | 1230.00 |
| NATROSOL™ PLUS 330 | 24.60 |
| (Mix 5 Minutes) | |
| TAMOL™ 165A | 55.76 |
| Triton™ CF-10 | 16.40 |
| AMP-95 | 4.10 |
| BYK-024 | 20.50 |
| TRONOX® 826S | 2885.58 |
| KATHON™ LX 1.5% | 14.76 |
| (Mix 15 Minutes) | |
| Total: | 4251.70 |

TABLE 14

Master Paint Formulations: Encor™ 379G

| | Formulation A | Formulation B | Formulation C | Formulation D | Formulation E | Formulation F | Formulation G | Formulation H |
|---|---|---|---|---|---|---|---|---|
| Common Grind (g) | 518.50 | 518.50 | 518.50 | 518.50 | 518.50 | 518.50 | 518.50 | 518.50 |
| Encor™ 379G (g) | 416.80 | 416.80 | 416.80 | 416.80 | 416.80 | 416.80 | 416.80 | 416.80 |
| Coalescent/ RFHA (g) | Texanol™ (11.69) | OE400 (12.15) | Citroflex™ 4 (12.61) | 0 | 0 | 0 | 0 | 0 |
| RFHA (g) | 0 | 0 | 0 | Ex 6 (14.21) | Ex 10 (15.82) | Ex 13-1 (12.15) | Ex 13-2 (14.00) | Ex 14 (13.30) |
| Acrysol™ RM-6000 (g) (Mix 10 Minutes) | 20.00 | 20.00 | 20.00 | 20.00 | 20.00 | 20.00 | 20.00 | 20.00 |

TABLE 14-continued

Master Paint Formulations: Encor™ 379G

| | Formulation A | Formulation B | Formulation C | Formulation D | Formulation E | Formulation F | Formulation G | Formulation H |
|---|---|---|---|---|---|---|---|---|
| Water | 94.68 | 94.44 | 94.89 | 93.08 | 91.74 | 95.32 | 93.56 | 93.98 |
| Acrysol™ RM-725 (g) (Final Mix 15 Minutes) | 6.50 | 6.50 | 6.50 | 6.50 | 6.50 | 6.50 | 6.50 | 6.50 |
| Total (g) | 1068.17 | 1068.39 | 1069.30 | 1069.09 | 1069.36 | 1069.27 | 1069.36 | 1069.07 |

TABLE 15

Stability of wet paint formulations: Encor™ 379G

| | Initial | | | 24 hr | | | | 1 Week | | | |
|---|---|---|---|---|---|---|---|---|---|---|---|
| Formulation | KU | pH | ICI (poise) | KU | Δ KU | ICI (poise) | pH | KU | Δ KU | ICI (poise) | pH |
| A | 95.3 | 8.63 | 1.092 | 97.0 | 1.7 | 1.12  | 8.64 | 97.5 | 2.2 | 1.064 | 8.51 |
| B | 94.2 | 8.62 | 1.252 | 96.8 | 2.6 | 1.083 | 8.63 | 95.6 | 1.4 | 1.277 | 8.49 |
| C | 94.5 | 8.63 | 1.102 | 97.9 | 3.4 | 1.078 | 8.63 | 97.1 | 2.6 | 1.064 | 8.50 |
| D | 94.6 | 8.57 | 1.064 | 97.4 | 2.8 | 1.092 | 8.59 | 97.5 | 2.9 | 1.275 | 8.50 |
| E | 93.4 | 8.57 | 1.148 | 98.1 | 4.7 | 1.120 | 8.56 | 98.2 | 4.8 | 1.247 | 8.44 |
| F | 93.4 | 8.52 | 1.073 | 95.7 | 2.3 | 0.983 | 8.64 | 96.0 | 2.6 | 1.073 | 8.49 |
| G | 93.7 | 8.57 | 1.116 | 97.3 | 3.6 | 1.242 | 8.56 | 97.7 | 4.0 | 1.087 | 8.41 |
| H | 94.0 | 8.54 | 1.167 | 96.7 | 2.7 | 1.111 | 8.58 | 97.5 | 3.5 | 1.097 | 8.42 |

Stormer viscosities were measured with a KU-2 viscometer by Brookfield. ICI viscosities were measured with a BYK CAP 2000 + viscometer.

TABLE 16

28-day König hardness: Encor™ 379G

| Formulation | Dry Time (1 Day) Hardness (sec) | Dry Time (7 Days) Hardness (sec) | Dry Time (14 Days) Hardness (sec) | Dry Time (21 Days) Hardness (sec) | Dry Time (28 Days) Hardness (sec) |
|---|---|---|---|---|---|
| A | 13 | 16 | 15 | 15 | 17 |
| B | 9  | 10 | 9  | 9  | 9  |
| C | 10 | 10 | 10 | 10 | 9  |
| D | 9  | 12 | 13 | 12 | 15 |
| E | 10 | 11 | 13 | 13 | 13 |
| F | 10 | 13 | 14 | 15 | 14 |
| G | 9  | 12 | 11 | 13 | 13 |
| H | 8  | 11 | 11 | 14 | 14 |

Drawdowns of the paints (3 mil wet on aluminum panels) were prepared for König testing. All drawdowns were stored in a controlled temperature room until use. König testing was done using BYK Gardner pendulum hardness tester. Reported values are the average of three measurements per panel.

TABLE 17

21-day block resistance: Encor™ 379G

| Formulation | Dry Time (1 Day) Block Resistance | Dry Time (7 Days) Block Resistance | Dry Time (14 Days) Block Resistance | Dry Time (21 Days) Block Resistance |
|---|---|---|---|---|
| A | 0 | 0 | 0 | 0 |
| B | 0 | 0 | 0 | 0 |
| C | 0 | 0 | 0 | 0 |
| D | 0 | 1 | 2 | 3 |
| E | 0 | 0 | 0 | 0 |
| F | 0 | 0 | 0 | 0 |

TABLE 17-continued 21-day block resistance: Encor™ 379G

| Formulation | Dry Time (1 Day) Block Resistance | Dry Time (7 Days) Block Resistance | Dry Time (14 Days) Block Resistance | Dry Time (21 Days) Block Resistance |
|---|---|---|---|---|
| G | 0 | 0 | 0 | 1 |
| H | 0 | 0 | 0 | 3 |

Drawdowns of the paints (6 mil wet on Form BH Leneta charts) were prepared for Block Resistance testing. All drawdowns were stored in a controlled temperature room until use. Testing was done based on ASTM method D4946. Reported values are the average of three measurements per panel.

TABLE 18

Common Grind formulation: Rhoplex™ HG-95P

| Component | Weight (g) |
|---|---|
| Water | 1025.00 |
| NATROSOL™ PLUS 330 (Mix 5 Minutes) | 12.30 |
| TAMOL™ 165A | 55.76 |
| Triton™ CF-10 | 16.40 |
| AMP-95 | 16.40 |
| BYK-024 | 20.50 |
| TRONOX® 826S | 2885.58 |
| KATHON™ LX 1.5% (Mix 15 Minutes) | 14.76 |
| Total: | 4046.70 |

TABLE 19

Master Paint Formulations: Rhoplex™ HG-95P

| | Formulation A | Formulation B | Formulation C | Formulation D | Formulation E | Formulation F | Formulation G | Formulation H |
|---|---|---|---|---|---|---|---|---|
| Common Grind (g) | 493.50 | 493.50 | 493.50 | 493.50 | 493.50 | 493.50 | 493.50 | 493.50 |
| Rhoplex™ HG-95P (g) | 486.80 | 486.80 | 486.80 | 486.80 | 486.80 | 486.80 | 486.80 | 486.80 |
| Coalescent (g) | Texanol™ (25.81) | OE400 (30.79) | Citroflex™ 4 (28.97) | 0 | 0 | 0 | 0 | 0 |
| RFHA (g) | 0 | 0 | 0 | Ex 6 (32.82) | Ex 10 (43.24) | Ex 13-1 (32.37) | Ex 13-2 (33.95) | Ex 14 (32.82) |
| Acrysol™ RM-2020 (g) (Mix 10 Minutes) | 20.00 | 20.00 | 20.00 | 20.00 | 20.00 | 20.00 | 20.00 | 20.00 |
| Water | 36.39 | 31.75 | 35.76 | 31.44 | 21.88 | 32.47 | 30.98 | 31.44 |
| Acrysol™ RM-725 (g) (Final Mix 15 Minutes) | 1.20 | 1.20 | 1.20 | 1.20 | 1.20 | 1.20 | 1.20 | 1.20 |
| Total (g) | 1063.70 | 1064.03 | 1066.24 | 1065.76 | 1066.61 | 1066.34 | 1066.44 | 1065.76 |

TABLE 20

Stability of wet paint formulations: Rhoplex HG-95P

| | Initial | | | 24 hr | | | | 1 Week | | | |
|---|---|---|---|---|---|---|---|---|---|---|---|
| Formulation | KU | pH | ICI (poise) | KU | Δ KU | ICI (poise) | pH* | KU | Δ KU | ICI (poise) | pH |
| A | 97.2 | 9.23 | 0.947 | 100.5 | 3.3 | 0.989 | 9.34 | 102.4 | 5.2 | 0.961 | 9.13 |
| B | 98.2 | 9.25 | 1.055 | 102.5 | 4.3 | 1.055 | 9.21 | 103.1 | 4.9 | 1.015 | 9.35 |
| C | 95.8 | 9.15 | 0.980 | 99.4 | 3.6 | 1.031 | 9.20 | 102.3 | 6.5 | 0.980 | 9.12 |
| D | 98.0 | 9.00 | 1.083 | 101.4 | 3.4 | 1.050 | 9.18 | 104.4 | 6.4 | 1.055 | 9.15 |
| E | 101.5 | 9.01 | 1.223 | 105.4 | 3.9 | 1.219 | 9.27 | 108.8 | 7.3 | 1.148 | 9.24 |
| F | 97.0 | 8.93 | 1.050 | 99.1 | 2.1 | 1.083 | 9.25 | 102.3 | 5.3 | 1.031 | 9.15 |
| G | 99.5 | 9.18 | 1.069 | 101.8 | 2.3 | 1.045 | 9.25 | 103.5 | 4.0 | 1.017 | 9.27 |
| H | 97.7 | 9.01 | 1.078 | 100.6 | 2.9 | 1.059 | 9.26 | 103.4 | 5.7 | 1.027 | 9.12 |

Stormer viscosities were measured with a KU-2 viscometer by Brookfield. ICI viscosities were measured with a BYK CAP 2000 + viscometer. *Measurement was taken at 72 hrs.

TABLE 21

28-day König hardness: Rhoplex HG-95P

| Formulation | Dry Time (1 Day) Hardness (sec) | Dry Time (7 Days) Hardness (sec) | Dry Time (14 Days) Hardness (sec) | Dry Time (21 Days) Hardness (sec) | Dry Time (28 Days) Hardness (sec) |
|---|---|---|---|---|---|
| A | 19 | 24 | 24 | 27 | 29 |
| B | 12 | 13 | 13 | 13 | 15 |
| C | 14 | 13 | 13 | 14 | 14 |
| D | 16 | 27 | 35 | 38 | 41 |
| E | 15 | 22 | 24 | 25 | 27 |
| F | 14 | 22 | 25 | 32 | 36 |
| G | 16 | 24 | 32 | 34 | 39 |
| H | 14 | 22 | 26 | 31 | 37 |

Drawdowns of the paints (3 mil wet on aluminum panels) were prepared for König testing. All drawdowns were stored in a controlled temperature room until use. König testing was done using BYK Gardner pendulum hardness tester. Reported values are the average of three measurements per panel.

TABLE 22

14-day block resistance: Rhoplex HG-95P

| Formulation | Dry Time (1 Day) Block Resistance | Dry Time (7 Days) Block Resistance | Dry Time (28 Days) Block Resistance |
|---|---|---|---|
| A | 2 | 6 | 6 |
| B | 3 | 5 | 5 |
| C | 3 | 5 | 6 |
| D | 8 | 9 | 9 |
| E | 7 | 9 | 9 |
| F | 6 | 9 | 9 |
| G | 7 | 9 | 9 |
| H | 8 | 9 | 9 |

Drawdowns of the paints (6 mil wet on Form BH Leneta charts) were prepared for Block Resistance testing. All drawdowns were stored in a controlled temperature room until use. Testing was done based on ASTM method D4946. Reported values are the average of three measurements per panel.

TABLE 23

| | Latex | | | | | | | |
|---|---|---|---|---|---|---|---|---|
| | Rhoplex™ SG-30 | | Acronal™ 296 D | | Encor™ 379 | | Rhoplex™ HG-95 | |
| Ex # | 4.0° C. (phr) | 2.0° C. (phr) | 4.0° C. (phr) | 2.0° C. (phr) | 4.0° C. (phr) | 2.0° C. (phr) | 4.0° C. (phr) | 2.0° C. (phr) |
| Texanol™ | 4.62 | 5.46 | 6.78 | 7.80 | 2.91 | 4.13 | 9.38 | 10.39 |
| OE400 | 4.82 | 5.68 | 6.51 | 7.53 | 3.04 | 4.33 | 11.38 | 12.56 |
| Citroflex™ 4 | 4.47 | 5.25 | 5.63 | 6.49 | 3.14 | 4.51 | 10.70 | 11.81 |
| Example 10-EE 13a | 6.45 | 7.64 | 7.37 | 8.51 | 3.85 | 5.46 | 16.01 | 17.68 |
| Example 14-EE 17a | 6.06 | 7.18 | 6.85 | 7.93 | 3.90 | 5.50 | 14.62 | 16.15 |

Parts per hundred resin (PHR) of Texanol™, OE400, Citroflex™ 4, or reactive film-hardening additive required to lower MFFT to 4.0° C. and 2.0° C. in Rhoplex™ SG-30, Acronal™ 296 D, Encor™ 379, and Rhoplex™ HG-95 model coating systems Minimum Film-Forming Temperature (MFFT) Screening: ASTM 02354-10e MFFT efficiency testing was based on ASTM D2354. The model instrument used was an MFFT-90 bar which allows samples to be tested from −10° C. to 90° C. For waterborne latexes, reaching a temperature of 2° C. is the primary goal. To reach that temperature, the MFFT bar was set to range from 0° C. to 18° C. This range is important since those Tg values for waterborne latexes somewhat correlate with their coinciding MFFT value. The higher the Tg value, the higher the MFFT value and vice versa. Neat commercial architectural latexes typically lie within this temperature range when testing for MFFT efficiency. Depending on the Tg of the material being tested, the range can be adjusted accordingly to determine the film's MFFT.

The ultimate goal for the final paint is to form a continuous film at a low temperature (2° C.). To achieve this, the MFFT of the neat latex material is first determined. If the neat latex material is above an MFFT of 2° C., we will add the reactive film-hardening additive at different phr (% additive based on latex solids) levels to allow the latex to reach 2° C. To reach that temperature, a linear regression of the phr levels is performed. This allows one to determine the appropriate amount of reactive film-hardening additive to add to the final paint formulation. In addition to the determined phr values from the MFFT screening, one additional phr is added to the final paint formulation to account for pigmentation.

Test Procedure:
1. Turn water source, MFFT instrument, and nitrogen source on in that order
2. Let MFFT instrument equilibrate ~15 minutes
3. Raise lid on the instrument and place the film caster (~6 WFT) at the cold end (0°) of the bar
4. Our film caster is sectioned into individual squares allowing us to test up to five latex samples at a time
5. Add samples to film caster
6. Draw down samples from cold end to the warm end (18° C.) of the MFFT bar
7. Lower the lid on the instrument
8. Samples will be ready to evaluate in approximately 1-2 hours
9. New MFFT bar instruments are equipped with a cursor. Moving the cursor to the MFFT point of a sample, the temperature value will be shown on a digital display

TABLE 24

Common Grind formulation: Rhoplex™ SG-30

| Component | Weight (g) |
|---|---|
| Water | 780.00 |
| NATROSOL™ PLUS 330 | 7.80 |
| (Mix 5 Minutes) | |
| TAMOL™ 165A | 35.36 |
| Triton™ CF-10 | 10.40 |
| AMP-95 | 10.40 |
| BYK-024 | 13.00 |
| TRONOX® 826S | 1829.88 |
| KATHON™ LX 1.5% | 9.36 |
| (Mix 15 Minutes) | |
| Total: | 2696.20 |

TABLE 25

Master Paint Formulations: Rhoplex™ SG-30

| | Formulation A | Formulation B | Formulation C | Formulation D | Formulation E |
|---|---|---|---|---|---|
| Common Grind (g) | 518.50 | 518.50 | 518.50 | 518.50 | 518.50 |
| Rhoplex™ SG-30 (g) | 450.30 | 450.30 | 450.30 | 450.30 | 450.30 |
| Coalescent (g) | Texanol™ (14.86) | OE400 (15.00) | Citroflex™ 4 (13.96) | 0 | 0 |
| RFHA (g) | 0 | 0 | 0 | Ex 10-EE 13a (19.36) | Ex 14-EE 17a (18.46) |
| Acrysol™ RM-6000 (g) | 20.00 | 20.00 | 20.00 | 20.00 | 20.00 |
| (Mix 10 Minutes) | | | | | |
| Water | 57.36 | 57.50 | 59.61 | 53.87 | 54.96 |
| Acrysol™ RM-725 (g) | 1.75 | 1.75 | 1.75 | 1.75 | 1.75 |
| (Final Mix 15 Minutes) | | | | | |
| Total (g) | 1062.77 | 1063.05 | 1064.12 | 1063.79 | 1063.97 |

TABLE 26

Stability of wet paint formulations: Rhoplex SG-30

| | Initial | | | 24 hr | | | | 1 Week | | | |
|---|---|---|---|---|---|---|---|---|---|---|---|
| Formulation | KU | pH | ICI (poise) | KU | Δ KU | ICI (poise) | pH | KU | Δ KU | ICI (poise) | pH |
| A | 95.6 | 9.38 | 1.064 | 100.8 | 5.2 | 1.073 | 9.41 | 103.2 | 7.6 | 1.144 | 9.37 |
| B | 95.6 | 9.37 | 1.041 | 100.6 | 5.0 | 1.108 | 9.42 | 103.7 | 8.1 | 1.158 | 9.40 |
| C | 95.1 | 9.37 | 0.989 | 99.8 | 4.7 | 1.031 | 9.43 | 103.0 | 7.9 | 1.116 | 9.39 |
| D | 97.1 | 9.43 | 1.331 | 101.1 | 4.0 | 1.134 | 9.44 | 105.0 | 7.9 | 1.195 | 9.33 |
| E | 96.9 | 9.35 | 1.106 | 100.1 | 3.2 | 1.139 | 9.41 | 104.9 | 8.0 | 1.162 | 9.47 |

Stormer viscosities were measured with a KU-2 viscometer by Brookfield. ICI viscosities were measured with a BYK CAP 2000 + viscometer.

TABLE 27

28-day König hardness: Rhoplex SG-30

| Formulation | Dry Time (1 Day) Hardness (sec) | Dry Time (7 Days) Hardness (sec) | Dry Time (14 Days) Hardness (sec) | Dry Time (21 Days) Hardness (sec) | Dry Time (28 Days) Hardness (sec) |
|---|---|---|---|---|---|
| A | 15 | 19 | 24 | 24 | 25 |
| B | 10 | 10 | 10 | 11 | 11 |
| C | 13 | 12 | 13 | 13 | 12 |
| D | 13 | 17 | 19 | 20 | 21 |
| E | 10 | 16 | 17 | 20 | 22 |

Drawdowns of the paints (3 mil wet on aluminum panels) were prepared for König testing. All drawdowns were stored in a controlled temperature room until use. König testing was done using BYK Gardner pendulum hardness tester. Reported values are the average of three measurements per panel.

TABLE 28

14-day block resistance: Rhoplex SG-30

| Formulation | Dry Time (1 Day) Block Resistance | Dry Time (7 Days) Block Resistance | Dry Time (14 Days) Block Resistance |
|---|---|---|---|
| A | 6 | 8 | 9 |
| B | 5 | 6 | 7 |
| C | 5 | 6 | 8 |
| D | 6 | 10 | 10 |
| E | 6 | 9 | 10 |

Drawdowns of the paints (6 mil wet on Form BH Leneta charts) were prepared for Block Resistance testing. All drawdowns were stored in a controlled temperature room until use. Testing was done based on ASTM method D4946. Reported values are the average of three measurements per panel.

TABLE 29

Common Grind formulation: Acronal™ 296D

| Component | Weight (g) |
|---|---|
| Water | 780.00 |
| NATROSOL™ PLUS 330 (Mix 5 Minutes) | 7.80 |
| TAMOL™ 165A | 35.36 |
| Triton™ CF-10 | 10.40 |
| AMP-95 | 10.40 |
| BYK-024 | 13.00 |
| TRONOX® 826S | 1829.88 |
| KATHON™ LX 1.5% (Mix 15 Minutes) | 9.36 |
| Total: | 2696.20 |

TABLE 30

Master Paint Formulations: Acronal™ 296D

| | Formulation A | Formulation B | Formulation C | Formulation D | Formulation E |
|---|---|---|---|---|---|
| Common Grind (g) | 518.50 | 518.50 | 518.50 | 518.50 | 518.50 |
| Acronal® 296D (g) | 432.00 | 432.00 | 432.00 | 432.00 | 432.00 |
| Coalescent (g) | Texanol™ (19.01) | OE400 (18.36) | Citroflex™ 4 (16.20) | 0 | 0 |
| RFHA (g) | 0 | 0 | 0 | Ex 10-EE 13a (20.52) | Ex 14-EE 17a (19.22) |
| Acrysol™ RM-6000 (g) (Mix 10 Minutes) | 20.00 | 20.00 | 20.00 | 20.00 | 20.00 |
| Water | 59.70 | 60.74 | 64.17 | 59.44 | 60.92 |
| Acrysol™ RM-725 (g) (Final Mix 15 Minutes) | 3.40 | 3.40 | 3.40 | 3.40 | 3.40 |
| Total (g) | 1052.61 | 1053.00 | 1054.27 | 1053.86 | 1054.05 |

TABLE 31

Stability of wet paint formulations: Acronal 296D

| | Initial | | | 24 hr | | | | 1 Week | | | |
|---|---|---|---|---|---|---|---|---|---|---|---|
| Formulation | KU | pH | ICI (poise) | KU | Δ KU | ICI (poise) | pH | KU | Δ KU | ICI (poise) | pH |
| A | 96.3 | 9.05 | 1.383 | 104.2 | 7.9 | 1.355 | 9.08 | 107.2 | 10.9 | 1.383 | 8.92 |
| B | 94.6 | 9.10 | 1.242 | 103.0 | 8.4 | 1.200 | 9.06 | 105.3 | 10.7 | 1.242 | 9.03 |
| C | 94.0 | 9.07 | 1.284 | 101.6 | 7.6 | 1.219 | 9.03 | 104.3 | 10.3 | 1.341 | 8.94 |

TABLE 31-continued

Stability of wet paint formulations: Acronal 296D

| Formulation | Initial KU | Initial pH | Initial ICI (poise) | 24 hr KU | 24 hr Δ KU | 24 hr ICI (poise) | 24 hr pH | 1 Week KU | 1 Week Δ KU | 1 Week ICI (poise) | 1 Week pH |
|---|---|---|---|---|---|---|---|---|---|---|---|
| D | 95.6 | 9.11 | 1.256 | 102.6 | 7.0 | 1.261 | 9.09 | 106.3 | 10.7 | 1.514 | 9.01 |
| E | 94.8 | 9.06 | 1.204 | 103.4 | 8.6 | 1.233 | 9.05 | 104.9 | 10.1 | 1.205 | 8.92 |

Stormer viscosities were measured with a KU-2 viscometer by Brookfield. ICI viscosities were measured with a BYK CAP 2000 + viscometer.

TABLE 32

28-day König hardness: Acronal 296D

| Formulation | Dry Time (1 Day) Hardness (sec) | Dry Time (7 Days) Hardness (sec) | Dry Time (14 Days) Hardness (sec) | Dry Time (14 Days) Hardness (sec) | Dry Time (28 Days) Hardness (sec) |
|---|---|---|---|---|---|
| A | 11 | 16 | 20 | 23 | 22 |
| B | 7 | 8 | 8 | 8 | 8 |
| C | 6 | 7 | 8 | 8 | 8 |
| D | 8 | 15 | 19 | 21 | 21 |
| E | 7 | 14 | 20 | 21 | 22 |

Drawdowns of the paints (3 mil wet on aluminum panels) were prepared for König testing. All drawdowns were stored in a controlled temperature room until use. König testing was done using BYK Gardner pendulum hardness tester. Reported values are the average of three measurements per panel.

TABLE 33

14-day block resistance: Acronal 296D

| Formulation | Dry Time (1 Day) Block Resistance | Dry Time (7 Days) Block Resistance | Dry Time (14 Days) Block Resistance |
|---|---|---|---|
| A | 0 | 1 | 3 |
| B | 0 | 0 | 0 |
| C | 0 | 0 | 0 |
| D | 4 | 7 | 8 |
| E | 4 | 7 | 8 |

Drawdowns of the paints (6 mil wet on Form BH Leneta charts) were prepared for Block Resistance testing. All drawdowns were stored in a controlled temperature room until use. Testing was done based on ASTM method D4946. Reported values are the average of three measurements per panel.

TABLE 34

Common Grind formulation: Encor™ 379G

| Component | Weight (g) |
|---|---|
| Water | 780.00 |
| NATROSOL™ PLUS 330 (Mix 5 Minutes) | 15.60 |
| TAMOL™ 165A | 35.36 |
| Triton™ CF-10 | 10.40 |
| AMP-95 | 2.60 |
| BYK-024 | 13.00 |
| TRONOX® 826S | 1829.88 |
| KATHON™ LX 1.5% (Mix 15 Minutes) | 9.36 |
| Total: | 2696.20 |

TABLE 35

Master Paint Formulations: Encor™ 379G

| | Formulation A | Formulation B | Formulation C | Formulation D | Formulation E |
|---|---|---|---|---|---|
| Common Grind (g) | 518.50 | 518.50 | 518.50 | 518.50 | 518.50 |
| Encor™ 379G (g) | 416.80 | 416.80 | 416.80 | 416.80 | 416.80 |
| Coalescent (g) | Texanol™ (11.69) | OE400 (12.15) | Citroflex™ 4 (12.61) | 0 | 0 |
| RFHA (g) | 0 | 0 | 0 | Ex 10-EE 13a (14.90) | Ex 14-EE 17a (14.90) |
| Acrysol™ RM-6000 (g) (Mix 10 Minutes) | 20.00 | 20.00 | 20.00 | 20.00 | 20.00 |
| Water | 94.68 | 94.44 | 94.89 | 92.27 | 92.42 |
| Acrysol™ RM-725 (g) (Final Mix 15 Minutes) | 6.50 | 6.50 | 6.50 | 6.50 | 6.50 |
| Total (g) | 1068.17 | 1068.39 | 1069.30 | 1068.97 | 1069.12 |

TABLE 36

Stability of wet paint formulations: Encor™ 379G

| Formulation | Initial KU | Initial pH | Initial ICI (poise) | 24 hr KU | 24 hr Δ KU | 24 hr ICI (poise) | 24 hr pH | 1 Week KU | 1 Week Δ KU | 1 Week ICI (poise) | 1 Week pH |
|---|---|---|---|---|---|---|---|---|---|---|---|
| A | 95.3 | 8.63 | 1.092 | 97.0 | 1.7 | 1.12 | 8.64 | 97.5 | 2.2 | 1.064 | 8.51 |
| B | 94.2 | 8.62 | 1.252 | 96.8 | 2.6 | 1.083 | 8.63 | 95.6 | 1.4 | 1.277 | 8.49 |
| C | 94.5 | 8.63 | 1.102 | 97.9 | 3.4 | 1.078 | 8.63 | 97.1 | 2.6 | 1.064 | 8.50 |

TABLE 36-continued

Stability of wet paint formulations: Encor™ 379G

| Formulation | Initial KU | pH | ICI (poise) | 24 hr KU | Δ KU | ICI (poise) | pH | 1 Week KU | Δ KU | ICI (poise) | pH |
|---|---|---|---|---|---|---|---|---|---|---|---|
| D | 95.0 | 8.59 | 1.530 | 97.7 | 2.7 | 1.191 | 8.61 | 98.4 | 3.4 | 1.130 | 8.48 |
| E | 95.3 | 8.61 | 1.111 | 97.6 | 2.3 | 1.073 | 8.60 | 97.6 | 2.3 | 1.073 | 8.60 |

Stormer viscosities were measured with a KU-2 viscometer by Brookfield. ICI viscosities were measured with a BYK CAP 2000 + viscometer.

TABLE 37

28-day König hardness: Encor™ 379G

| Formulation | Dry Time (1 Day) Hardness (sec) | Dry Time (7 Days) Hardness (sec) | Dry Time (14 Days) Hardness (sec) | Dry Time (21 Days) Hardness (sec) | Dry Time (28 Days) Hardness (sec) |
|---|---|---|---|---|---|
| A | 13 | 16 | 15 | 15 | 17 |
| B | 9 | 10 | 9 | 9 | 10 |
| C | 10 | 10 | 10 | 10 | 9 |
| D | 10 | 11 | 15 | 14 | 15 |
| E | 9 | 11 | 13 | 13 | 14 |

Drawdowns of the paints (3 mil wet on aluminum panels) were prepared for König testing. All drawdowns were stored in a controlled temperature room until use. König testing was done using BYK Gardner pendulum hardness tester. Reported values are the average of three measurements per panel.

TABLE 38

21-day block resistance: Encor™ 379G

| Formulation | Dry Time (1 Day) Block Resistance | Dry Time (7 Days) Block Resistance | Dry Time (14 Days) Block Resistance | Dry Time (21 Days) Block Resistance |
|---|---|---|---|---|
| A | 0 | 0 | 0 | 0 |
| B | 0 | 0 | 0 | 0 |
| C | 0 | 0 | 0 | 0 |
| D | 0 | 1 | 0 | 1 |
| E | 0 | 0 | 1 | 5 |

Drawdowns of the paints (6 mil wet on Form BH Leneta charts) were prepared for Block Resistance testing. All drawdowns were stored in a controlled temperature room until use. Testing was done based on ASTM method D4946. Reported values are the average of three measurements per panel.

TABLE 39

Common Grind formulation: Rhoplex HG-95P

| Component | Weight (g) |
|---|---|
| Water | 650.00 |
| NATROSOL™ PLUS 330 (Mix 5 Minutes) | 7.80 |
| TAMOL™ 165A | 35.36 |
| Triton™ CF-10 | 10.40 |
| AMP-95 | 10.40 |
| BYK-024 | 13.00 |
| TRONOX® 826S | 1829.88 |
| KATHON™ LX 1.5% (Mix 15 Minutes) | 9.36 |
| Total: | 2566.20 |

TABLE 40

Master Paint Formulations: Rhoplex™ HG-95P

| | Formulation A | Formulation B | Formulation C | Formulation D | Formulation E |
|---|---|---|---|---|---|
| Common Grind (g) | 493.50 | 493.50 | 493.50 | 493.50 | 493.50 |
| Rhoplex™ HG-95P (g) | 486.80 | 486.80 | 486.80 | 486.80 | 486.80 |
| Coalescent (g) | Texanol™ (25.81) | OE400 (30.79) | Citroflex™ 4 (28.97) | 0 | 0 |
| RFHA (g) | 0 | 0 | 0 | Ex 10-EE 13a (42.33) | Ex 14-EE 17a (38.71) |
| Acrysol™ RM-2020 (g) (Mix 10 Minutes) | 20.00 | 20.00 | 20.00 | 20.00 | 20.00 |
| Water | 36.39 | 31.75 | 35.76 | 21.73 | 25.72 |
| Acrysol™ RM-725 (g) (Final Mix 15 Minutes) | 1.20 | 1.20 | 1.20 | 1.20 | 1.20 |
| Total (g) | 1063.70 | 1064.03 | 1066.24 | 1065.56 | 1065.93 |

TABLE 41

Stability of wet paint formulations: Rhoplex HG-95P

| Formulation | Initial KU | pH | ICI (poise) | 24 hr KU | Δ KU | ICI (poise) | pH* | 1 Week KU | Δ KU | ICI (poise) | pH |
|---|---|---|---|---|---|---|---|---|---|---|---|
| A | 97.2 | 9.23 | 0.947 | 100.5 | 3.3 | 0.989 | 9.34 | 102.4 | 5.2 | 0.961 | 9.13 |
| B | 98.2 | 9.25 | 1.055 | 102.5 | 4.3 | 1.055 | 9.21 | 103.1 | 4.9 | 1.015 | 9.35 |
| C | 95.8 | 9.15 | 0.980 | 99.4 | 3.6 | 1.031 | 9.20 | 102.3 | 6.5 | 0.980 | 9.12 |

TABLE 41-continued

Stability of wet paint formulations: Rhoplex HG-95P

| Formulation | Initial | | | 24 hr | | | | 1 Week | | | |
|---|---|---|---|---|---|---|---|---|---|---|---|
| | KU | pH | ICI (poise) | KU | Δ KU | ICI (poise) | pH* | KU | Δ KU | ICI (poise) | pH |
| D | 103.2 | 9.23 | 1.181 | 106.6 | 3.4 | 1.237 | 9.30 | 110.5 | 7.3 | 1.139 | 9.22 |
| E | 101.8 | 9.24 | 1.209 | 104.7 | 2.9 | 1.378 | 9.32 | 108.1 | 6.3 | 1.214 | 9.38 |

Stormer viscosities were measured with a KU-2 viscometer by Brookfield. ICI viscosities were measured with a BYK CAP 2000 + viscometer.
*Measurement was taken at 72 hrs.

TABLE 42

28-day König hardness: Rhoplex HG-95P

| Formulation | Dry Time (1 Day) Hardness (sec) | Dry Time (7 Days) Hardness (sec) | Dry Time (14 Days) Hardness (sec) | Dry Time (21 Days) Hardness (sec) | Dry Time (28 Days) Hardness (sec) |
|---|---|---|---|---|---|
| A | 19 | 24 | 24 | 27 | 29 |
| B | 12 | 13 | 13 | 13 | 15 |
| C | 14 | 13 | 13 | 14 | 14 |
| D | 14 | 22 | 26 | 29 | 32 |
| E | 13 | 23 | 30 | 32 | 40 |

Drawdowns of the paints (3 mil wet on aluminum panels) were prepared for König testing. All drawdowns were stored in a controlled temperature room until use. König testing was done using BYK Gardner pendulum hardness tester. Reported values are the average of three measurements per panel.

TABLE 43

14-day block resistance: Rhoplex HG-95P

| Formulation | Dry Time (1 Day) Block Resistance | Dry Time (7 Days) Block Resistance | Dry Time (14 Days) Block Resistance |
|---|---|---|---|
| A | 2 | 6 | 6 |
| B | 3 | 5 | 5 |
| C | 3 | 5 | 6 |
| D | 7 | 8 | 9 |
| E | 7 | 8 | 9 |

Drawdowns of the paints (6 mil wet on Form BH Leneta charts) were prepared for Block Resistance testing. All drawdowns were stored in a controlled temperature room until use. Testing was done based on ASTM method D4946. Reported values are the average of three measurements per panel.

The invention has been described in detail with reference to the embodiments disclosed herein, but it will be understood that variations and modifications can be effected within the spirit and scope of the invention.

We claim:

1. A coating composition comprising:
   a. at least one latex compound; and
   b. at least one aromatic enol ether having Formula I:

$$R^{1b}O-\overset{A}{\diagup}=\diagdown-O-R^{1a}$$ (I)

wherein:

A is $(C_{8-20})$ alkylaryl;

$R^{1a}$ and $R^{1b}$ are independently

[structures showing $-CH_2CH_2-O-[CH_2CH_2O]_n-R^4$ or $-CH_2-C(CH_3)_2-O-[...]_n-R^4$]
or ;

each $R^4$ is independently, hydrogen, $(C_{1-12})$alkyl, $(C_{2-12})$ alkenyl or $-C(O)R^5$;

each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;

each $R^6$ is $(C_{1-4})$alkoxy, or oxo; and each n is independently an integer from 1 to 15.

2. The aromatic enol ether of claim 1 wherein A is 1,2-, 1,3-, or 1,4-disubstituted phenyl.

3. The aromatic enol ether of claim 1 wherein $R^4$ is hydrogen or an ethyl group.

4. The aromatic enol ether of claim 1 wherein, n is an integer from 1 to 4.

5. The aromatic enol ether of claim 1 wherein the composition has a volatile organic content of less than 50 wt % according to ASTM D6886.

6. The coating composition of claim 1 wherein said at least one latex compound is an acrylic polymer, a vinyl acrylic polymer, a styrene butadiene polymer or a styrene acrylic latex polymer, or a mixture thereof.

7. The coating composition of claim 6 wherein said at least one latex compound has a Tg in the range of from about −20° C. to about 100° C.

8. The coating composition of claim 1 wherein said at least one latex compound is a styrene, methyl acrylate, methyl methacrylate, ethyl acrylate, ethyl methacrylate, butyl acrylate, butyl methacrylate, isobutyl acrylate, isobutyl methacrylate, ethylhexyl acrylate, 2-ethylhexyl methacrylate, 2-ethylhexyl acrylate, isoprene, octyl acrylate, octyl methacrylate, iso-octyl acrylate, iso-octyl methacrylate, acrylic acid, methacrylic acid, itaconic acid, crotonic acid, O-methyl styrene, vinyl naphthalene, vinyl toluene, chloromethyl styrene, hydroxyethyl (meth)acrylate, hydroxypropyl (meth)acrylate, acrylonitrile, glycidyl methacrylate, acetoacetoxyethyl methacrylate, acetoacetoxy ethyl acrylate, vinyl chloride, vinylidene chloride, vinyl acetate, butyl acrylamide, or ethyl acrylamide polymer or mixture thereof.

9. A method of improving the performance properties of a cured paint without contributing to the volatile organic content of the paint formula comprising adding an aromatic enol ether to said paint, wherein said aromatic enol ether has a Formula I, $$R^{1b}O-\overset{A}{\diagup}=\diagdown-O-R^{1a}$$ (I)

wherein: A is $(C_{8-20})$ alkylaryl;
$R^{1a}$ and $R^{1b}$ are independently
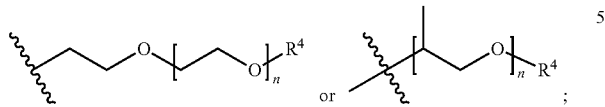
each $R^4$ is independently $(C_{1-12})$alkyl, or —C(O)$R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 1.
* * * * *